(12) United States Patent
Sagoh

(10) Patent No.: US 9,778,379 B2
(45) Date of Patent: Oct. 3, 2017

(54) PHOTON-COUNTING X-RAY CT APPARATUS AND PHOTON-COUNTING X-RAY DIAGNOSTIC APPARATUS

(71) Applicant: Toshiba Medical Systems Corporation, Otawara-shi (JP)

(72) Inventor: Tomoe Sagoh, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/942,363

(22) Filed: Nov. 16, 2015

(65) Prior Publication Data

US 2016/0070005 A1 Mar. 10, 2016

Related U.S. Application Data

(63) Continuation of application No. PCT/JP2015/067210, filed on Jun. 15, 2015.

(30) Foreign Application Priority Data

Jun. 16, 2014 (JP) ................................. 2014-123752

(51) Int. Cl.
*G01T 1/17* (2006.01)
*G01T 1/208* (2006.01)
(Continued)

(52) U.S. Cl.
CPC .............. *G01T 1/208* (2013.01); *A61B 6/032* (2013.01); *A61B 6/035* (2013.01); *A61B 6/4241* (2013.01);
(Continued)

(58) Field of Classification Search
None
See application file for complete search history.

(56) References Cited

U.S. PATENT DOCUMENTS 4,591,984 A * 5/1986 Mori ....................... G01T 1/171
250/363.02
2011/0216878 A1 9/2011 Roessl
(Continued)

FOREIGN PATENT DOCUMENTS

JP 07-280945 A 10/1995
JP 2000-023965 A 1/2000
(Continued)

OTHER PUBLICATIONS

International Search Report dated Aug. 25, 2015 for PCT/JP2015/067210 filed on Jun. 15, 2015 with English Translation of Categories.

(Continued)

*Primary Examiner* — Edwin Gunberg
(74) *Attorney, Agent, or Firm* — Oblon, McClelland, Maier & Neustadt, L.L.P.

(57) ABSTRACT

A photon-counting X-ray computed tomography (CT) apparatus of an embodiment includes photon-counting CT detection circuitry, integral CT detection circuitry, switching circuitry, and a feedback capacitance. Photon-counting CT detection circuitry outputs count values for respective energy bins, based on voltage pulses output from a feedback capacitance with electric charges output from an X-ray detection element configured to detect incident X-rays. Integral CT detection circuitry outputs an integral value, based on the voltage pulses output from the feedback capacitance with the electric charges output from the X-ray detection element. Switching circuitry switches between a case of transmitting the electric charges output from the X-ray detection element to the photon-counting CT detection circuitry and a case of transmitting the electric charges output from the X-ray detection element to the integral CT detection circuitry. The feedback capacitance is connected with the photon-counting CT detection circuitry and the integral CT detection circuitry in parallel.

12 Claims, 15 Drawing Sheets

(51) Int. Cl.
*A61B 6/03* (2006.01)
*G01T 1/18* (2006.01)
*G01T 1/20* (2006.01)
*A61B 6/00* (2006.01)

(52) U.S. Cl.
CPC .................. *G01T 1/17* (2013.01); *G01T 1/18* (2013.01); *G01T 1/2018* (2013.01)

(56) References Cited

U.S. PATENT DOCUMENTS

| | | |
|---|---|---|
| 2012/0032085 A1 | 2/2012 | Baeumer et al. |
| 2013/0010921 A1 | 1/2013 | Sagoh et al. |
| 2015/0316663 A1* | 11/2015 | Herrmann ............... G01T 1/247 382/132 |

FOREIGN PATENT DOCUMENTS

| | | |
|---|---|---|
| JP | 2012-509697 A | 4/2012 |
| JP | 2012-524255 A | 10/2012 |
| JP | 2013-000227 A | 1/2013 |
| JP | 2014-014445 A | 1/2014 |

OTHER PUBLICATIONS

Written Opinion dated Aug. 25, 2015 for PCT/JP2015/067210 filed on Jun. 15, 2015.

* cited by examiner

PHOTON-COUNTING X-RAY CT APPARATUS AND PHOTON-COUNTING X-RAY DIAGNOSTIC APPARATUS

CROSS-REFERENCE TO RELATED APPLICATIONS

This application is a continuation of PCT international application Ser. No. PCT/JP2015/067210 filed on Jun. 15, 2015 which designates the United States, incorporated herein by reference, and which claims the benefit of priority from Japanese Patent Application No. 2014-123752, filed on Jun. 16, 2014, the entire contents of which are incorporated herein by reference.

FIELD

Embodiments described herein relate generally to a photon-counting X-ray computed tomography (CT) apparatus and a photon-counting X-ray diagnostic apparatus.

BACKGROUND

Integral X-ray CT apparatuses and integral X-ray diagnostic apparatuses detect X-rays transmitted through a subject and X-rays scattered by the subject with a plurality of X-ray detection elements included in an X-ray detector. The X-ray detection elements convert the incident X-rays into electric charges, and output the electric charges to a data acquisition system (DAS). Integral X-ray CT apparatuses and integral X-ray diagnostic apparatuses generate a fluoroscopic image, a tomographic image, and a three-dimensional image, and the like, of the subject based on the electric charges collected by the data acquisition system.

The data acquisition system included in the integral X-ray CT apparatus and the integral X-ray diagnostic apparatus acquire an integral value of the energy of the X-rays detected by the X-ray detection elements. Specifically, all the energies of the X-rays detected by the X-ray detection elements are integrated in the integral X-ray CT apparatus and the integral X-ray diagnostic apparatus. For this reason, information of the X-ray having relatively low energy is buried, in the integral X-ray CT apparatus and the integral X-ray diagnostic apparatus. In addition, the energy spectrums of the X-rays for the respective detection circuitry may be shifted from each other due to variations in feedback capacitances of the detection circuitry connected to the X-ray detection elements.

However, the integral X-ray CT apparatus and the integral X-ray diagnostic apparatus cannot specify the energy for each electric charge and correct the energy spectrum of the X-rays for each detection circuitry, because the detection circuitry connected to the X-ray detection elements integrate the electric charges in the feedback capacitance. For this reason, the integral X-ray CT apparatus and the integral X-ray diagnostic apparatus may cause deterioration in image quality due to artifacts caused by beam hardening phenomenon or decrease in contrast resolution in a soft tissue.

DETAILED DESCRIPTION

A photon-counting X-ray computed tomography (CT) apparatus of an embodiment includes photon-counting CT detection circuitry, integral CT detection circuitry, switching circuitry, and a feedback capacitance. Photon-counting CT detection circuitry outputs count values for respective energy bins, based on voltage pulses output from a feedback capacitance with electric charges output from an X-ray detection element configured to detect incident X-rays. Integral CT detection circuitry outputs an integral value, based on the voltage pulses output from the feedback capacitance with the electric charges output from the X-ray detection element. Switching circuitry switches between a case of transmitting the electric charges output from the X-ray detection element to the photon-counting CT detection circuitry and a case of transmitting the electric charges output from the X-ray detection element to the integral CT detection circuitry. The feedback capacitance is connected with the photon-counting CT detection circuitry and the integral CT detection circuitry in parallel.

The following is explanation of a photon-counting X-ray CT apparatus and a photon-counting X-ray diagnostic apparatus according to embodiments with reference to drawings.

First Embodiment

Figure 1:
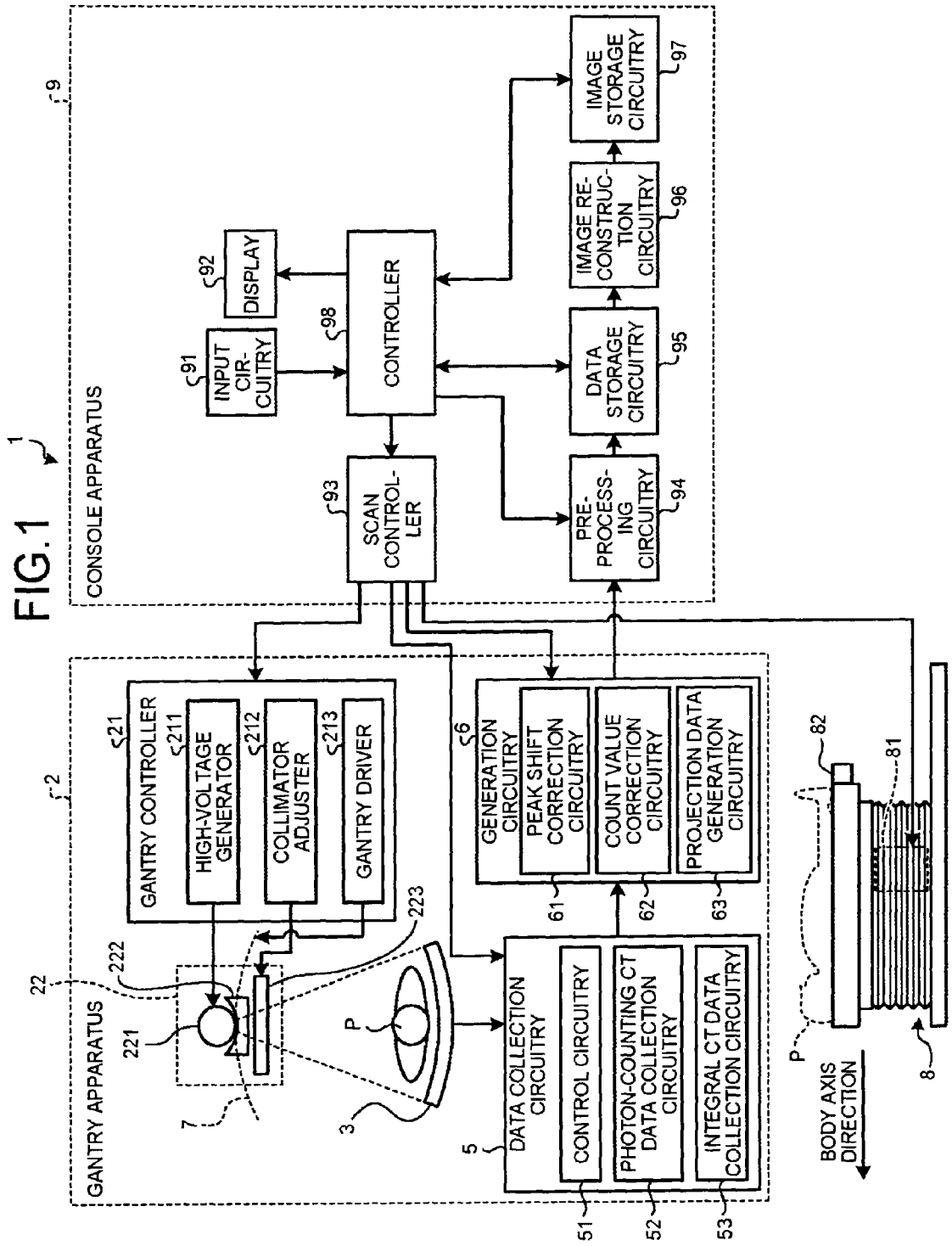
FIG. 1 is a diagram illustrating a configuration of a photon-counting X-ray CT apparatus according to a first embodiment.
Figure 2:
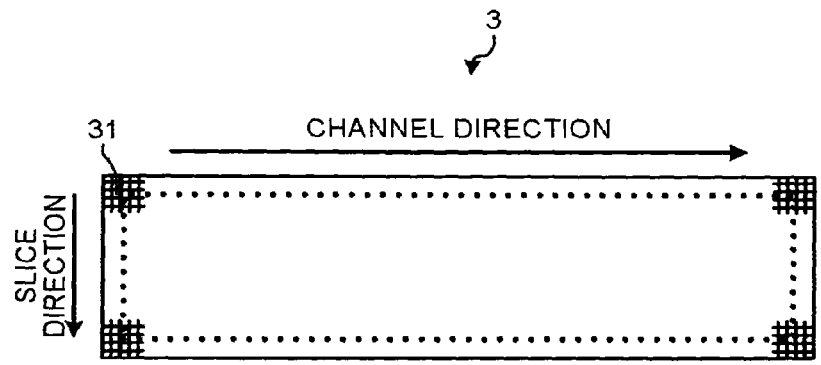
FIG. 2 is a diagram illustrating an example of an X-ray detector according to the first embodiment.
Figure 3:
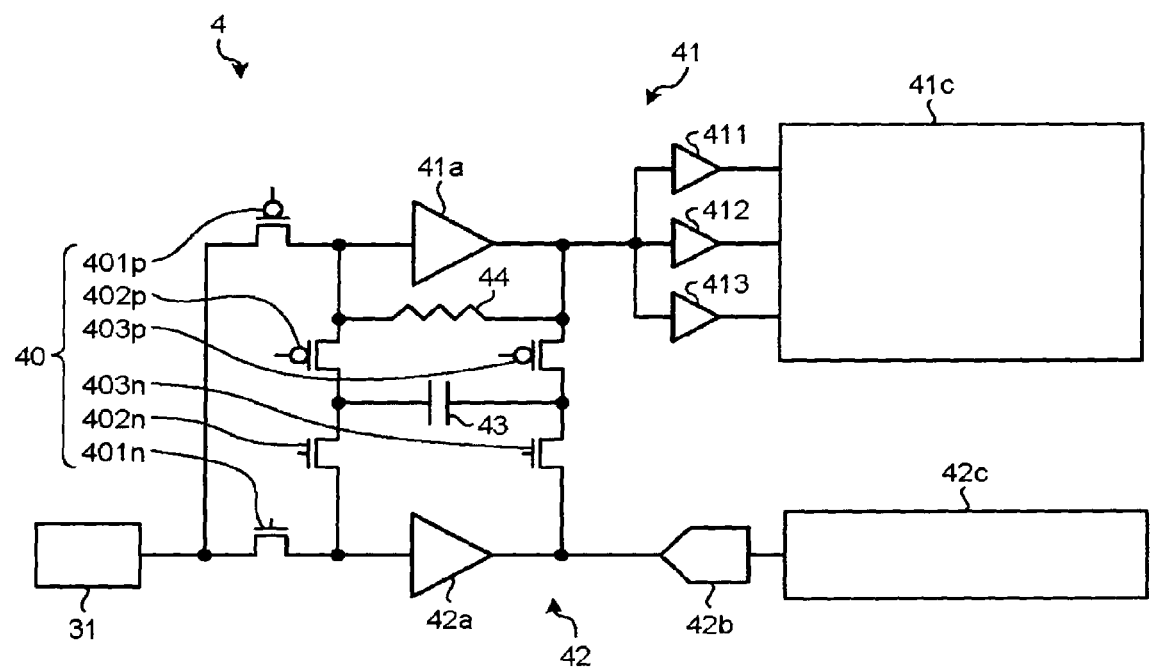
FIG. 3 is a diagram illustrating an example of detection circuitry according to the first embodiment.

First, the following is explanation of the configuration of a photon-counting X-ray CT apparatus 1 according to a first embodiment, with reference to FIG. 1, FIG. 2, and FIG. 3. FIG. 1 is a diagram illustrating the configuration of the photon-counting X-ray CT apparatus 1 according to the first embodiment. FIG. 2 is a diagram illustrating an example of an X-ray detector 3 according to the first embodiment. FIG. 3 is a diagram illustrating an example of detection circuitry 4 according to the first embodiment. As illustrated in FIG. 1, the photon-counting X-ray CT apparatus 1 includes a gantry apparatus 2, a couch apparatus 8, and a console apparatus 9. The configuration of the photon-counting X-ray CT apparatus 1 is not limited to the following configuration.

The gantry apparatus 2 irradiates a subject P with X-rays, and collects projection data, which will be described later. The gantry apparatus 2 includes a gantry controller 21, an X-ray generator 22, an X-ray detector 3, a data collection circuitry 5, a generation circuitry 6, and a rotating frame 7.

The gantry controller 21 controls, under the control of a scan controller 93 described later, the operations of the X-ray generator 22 and the rotating frame 7. The gantry controller 21 includes a high-voltage generator 211, a collimator adjuster 212, and a gantry driver 213. The high-voltage generator 211 supplies a tube voltage to an X-ray tube 221 described later. The collimator adjuster 212, by adjusting the aperture and position of a collimator 223, adjusts the irradiation range of the X-rays with which the X-ray generator 22 irradiates the subject P. For example, the collimator adjuster 212, by adjusting the aperture of the collimator 223, adjusts the irradiation range of the X-rays, more specifically, the fan angle and cone angle of the X-rays. The gantry driver 213, by rotatively driving the rotating frame 7, rotates the X-ray generator 22 and the X-ray detector 3 in a circular path centered on the subject P.

The X-ray generator 22 generates X-rays with which the subject P is irradiated. The X-ray generator 22 includes the X-ray tube 221, a wedge 222, and the collimator 223. The X-ray tube 221 generates beam-shaped X-rays with which the subject P is irradiated, by the tube voltage supplied from the high-voltage generator 211. The X-ray tube 221 is a vacuum tube that generates the beam-shaped X-rays having an expanse in a circular cone and pyramid shape along the direction of body axis of the subject P. The beam-shaped X-rays are also referred to as a cone beam. The X-ray tube 221 irradiates the subject P with the cone beam along with the rotation of the rotating frame 7. The wedge 222 is an X-ray filter to adjust the X-ray dosage of the X-rays emitted from the X-ray tube 221. The collimator 223 is a slit to narrow down the irradiation range of the X-rays for which the X-ray dosage has been adjusted by the wedge 222, by the control of the collimator adjuster 212.

As illustrated in FIG. 2, the X-ray detector 3 is a multi-row detector including a plurality of X-ray detection elements 31 arranged in a channel direction and a slice direction. The channel direction is the circumferential direction of the rotating frame 7, and the slice direction is the body axis direction of the subject P. Each of the X-ray detection elements 31 includes a scintillator and a photodiode. Each of the X-ray detection elements 31 converts the incident X-rays into light by the scintillator, and converts the light into an electric charge by the photodiode. The electric charge is output to a detection circuitry described later. The X-ray detector including the X-ray detection elements 31 each including a scintillator and a photodiode is referred to as an indirect conversion detector.

The X-ray detector 3 may be a direct conversion detector. The direct conversion detector is a detector that converts the photons, which have entered the X-ray detection elements 31, into electrical charges directly. The electrical charges output from the X-ray detection elements 31 are output by at least one of the running of electrons caused by the incident photons toward a collecting electrode of positive electric potential and the running of holes caused by the incident photons toward a collecting electrode of negative electric potential. In the case of a direct conversion detector, the X-ray detection elements 31 are of cadmium telluride (CdTe) based semiconductor elements, for example.

As illustrated in FIG. 3, the detection circuitry 4 includes switching circuitry 40, photon-counting CT detection circuitry 41, and integral CT detection circuitry 42. Each of the X-ray detection elements 31 is installed with detection circuitry 4.

As illustrated in FIG. 3, the switching circuitry 40 includes six metal oxide semiconductor field effect transistors (MOSFET). Specifically, the switching circuitry 40 includes an n-type MOSFET 401$n$, an n-type MOSFET 402$n$, and an n-type MOSFET 403$n$, a p-type MOSFET 401$p$, a p-type MOSFET 402$p$, and a p-type MOSFET 403$p$.

The switching circuitry 40 receives a switching signal described later, to switch each of the six MOSFETs described above between a conductive state and a non-conductive state. In this manner, the switching circuitry 40 switches between the case where the electric charges output from the X-ray detection element 31 are transmitted to the photon-counting CT detection circuitry 41 and the case where the electric charges output from the X-ray detection element 31 are transmitted to the integral CT detection circuitry 42. The switching circuitry 40 may switch, in each view, between the case where the electric charges output from the X-ray detection element 31 are transmitted to the photon-counting CT detection circuitry 41 and the case where the electric charges output from the X-ray detection element 31 are transmitted to the integral CT detection circuitry 42.

As illustrated in FIG. 3, the photon-counting CT detection circuitry 41 includes a first amplifier 41$a$, a first counter 41$c$, a feedback capacitance 43, and a resistor 44. The input terminal of the first amplifier 41$a$ is connected to the X-ray detection element 31 via the p-type MOSFET 401$p$. The input terminal of the first amplifier 41$a$ is also connected to a terminal of the resistor 44 on the X-ray detection element 31 side. The output terminal of the first amplifier 41$a$ is connected to the first counter 41$c$ via a comparator 411, a comparator 412, and a comparator 413. The output terminal of the first amplifier 41$a$ is also connected to a terminal of the resistor 44 on the first counter 41$c$ side. A terminal of the feedback capacitance 43 on the X-ray detection element 31 side is connected with the terminal of the resistor 44 on the X-ray detection element 31 side, via the p-type MOSFET 402$p$. A terminal of the feedback capacitance 43 on the first counter 41$c$ side is connected with the terminal of the resistor 44 on the first counter 41$c$ side, via the p-type MOSFET 403$p$. Specifically, the feedback capacitance 43 and the resistor 44 are connected to the first amplifier 41$a$ in parallel. In other words, the feedback capacitance 43 and the resistor 44 are connected to the photon-counting CT detection circuitry 41 in parallel. The input terminals of the comparator 411, the comparator 412, and the comparator 413 are connected to the output terminal of the first amplifier 41$a$, and the output terminals of the comparator 411, the comparator 412, and the comparator 413 are connected to the input terminal of the first counter 41$c$.

As illustrated in FIG. 3, the integral CT detection circuitry 42 includes a second amplifier 42$a$, a second counter 42$c$, and the feedback capacitance 43. The input terminal of the second amplifier 42$a$ is connected to the X-ray detection element 31 via the n-type MOSFET 401$n$. The input terminal of the second amplifier 42$a$ is also connected to the terminal of the feedback capacitance 43 on the X-ray detection element 31 side via the n-type MOSFET 402n. The output terminal of the second amplifier 42a is connected to the second counter 42c via an analog-to-digital (A/D) converter 42b. Specifically, the feedback capacitance 43 is connected to the second amplifier 42a in parallel. In other words, the feedback capacitance 43 and the resistor 44 are connected to the integral CT detection circuitry 42 in parallel. The output terminal of the second amplifier 42a is also connected to a terminal of the feedback capacitance 43 on the second counter 42c side via the n-type MOSFET 403n.

The photon-counting CT detection circuitry 41 outputs count values for respective energy bins, based on a voltage pulse that is output from the feedback capacitance 43 with the electric charges output from the X-ray detection element 31 that detects the incident X-rays. Specifically, the photon-counting CT detection circuitry 41 operates as explained in the following. The first amplifier 41a amplifies the voltage generated by the electric charges output from the X-ray detection element 31. The feedback capacitance 43 outputs a voltage pulse based on the voltage amplified by the first amplifier 41a. Respective thresholds are set for the comparator 411, the comparator 412, and the comparator 413. Each of the comparator 411, the comparator 412, and the comparator 413 outputs an electrical signal, when the intensity of the voltage pulse received by the comparator exceeds its threshold. The first counter 41c counts the respective electrical signals that are output from the comparator 411, the comparator 412, and the comparator 413. Specifically, the first counter 41c counts the voltage pulses output from the feedback capacitance 43 based on the electric charges output from the X-ray detection element 31, for each of a plurality of energy bins that are set on the energy spectrum of the X-rays.

The integral CT detection circuitry 42 outputs an integral value based on the voltage pulses output from the feedback capacitance 43 with the electric charges output from the X-ray detection element 31. Specifically, the integral CT detection circuitry 42 operates as explained in the following. The second amplifier 42a amplifies the voltage generated by the electric charges output from the X-ray detection element 31. The feedback capacitance 43 outputs a voltage pulse based on the voltage amplified by the second amplifier 42a. This voltage pulse includes the voltages based on all electric charges output from the X-ray detection element 31 in each view. The A/D converter 42b converts the received voltage pulse into a digital electrical signal and outputs the digital electrical signal. The second counter 42c counts the electrical signals that are output from the A/D converter 42b. Specifically, the second counter 42c counts the voltage pulses that are output from the feedback capacitance 43 based on the electric charges output from the X-ray detection element 31.

The resistor 44 functions to discharge the electric charges accumulated in the feedback capacitance 43, to prevent saturation of the feedback capacitance 43.

As illustrated in FIG. 1, the data collection circuitry 5 includes control circuitry 51, a photon-counting CT data collection circuitry 52, and an integral CT data collection circuitry 53.

The control circuitry 51 transmits switching signals to the switching circuitry 40. Specifically, the control circuitry 51 transmits switching signals to the gate terminals of the six MOSFETs described above. The switching signals include, in each view, a photon-counting CT ON signal to control the switching circuitry 40 to transmit the electric charges output from the X-ray detection element 31 to the photon-counting CT detection circuitry 41, and an integral CT ON signal to control the switching circuitry 40 to transmit the electric charges output from the X-ray detection element 31 to the integral CT detection circuitry 42. In the following explanation, the photon-counting CT ON signal may be referred to as PC ON signal, and the integral CT ON signal may be referred to as CT ON signal.

When the control circuitry 51 transmits a photon-counting CT ON signal to the switching circuitry 40, the n-type MOSFET 401n, the n-type MOSFET 402n, and the n-type MOSFET 403n are changed to a non-conductive state, and the p-type MOSFET 401p, the p-type MOSFET 402p, and the p-type MOSFET 403p are changed to a conductive state. In this manner, the electric charges output from the X-ray detection element 31 are transmitted to the photon-counting CT detection circuitry 41.

When the control circuitry 51 transmits an integral CT ON signal to the switching circuitry 40, the n-type MOSFET 401n, the n-type MOSFET 402n, and the n-type MOSFET 403n are changed to the conductive state, and the p-type MOSFET 401p, the p-type MOSFET 402p, and the p-type MOSFET 403p are changed to the non-conductive state. In this manner, the electric charges output from the X-ray detection element 31 are transmitted to the integral CT detection circuitry 42.

The photon-counting CT data collection circuitry 52 collects the count values of the first counter 41c, when the electric charges output from the X-ray detection element 31 are transmitted to the photon-counting CT detection circuitry 41 by the switching circuitry 40. The count value collected by the photon-counting CT data collection circuitry 52 is transmitted to the generation circuitry 6 described later. As described above, the count values of the first counter 41c are results of counting the voltage pulses that are output from the feedback capacitance 43 for the respective energy bins that are set on the energy spectrum of the X-rays.

The integral CT data collection circuitry 53 collects the count value of the second counter 42c, when the electric charges output from the X-ray detection element 31 are transmitted to the integral CT detection circuitry 42 by the switching circuitry 40. The count value collected by the integral CT data collection circuitry 53 is transmitted to the generation circuitry 6 described later. As described above, the count value of the second counter 42c is a result of counting the voltage pulses that are output from the feedback capacitance 43 regardless of the energy bins that are set on the energy spectrum of the X-rays.

The generation circuitry 6 includes a peak shift correction circuitry 61, a count value correction circuitry 62, and a projection data generation circuitry 63. The peak shift correction circuitry 61 is also referred to as second correction circuitry. The count value correction circuitry 62 is also referred to as first correction circuitry.

The peak shift correction circuitry 61 adds a certain energy value to the energy of the photons detected by the photon-counting CT detection circuitry 41 such that a count value that is output from the photon-counting CT detection circuitry 41 in an energy bin of the energy spectrum of the X-rays made incident on the X-ray detection element 31 falls within a predetermined range including a count value output from the photon-counting CT detection circuitry 41 in an energy bin including the peak generated by the characteristic X-rays of a reference X-ray energy spectrum. Specifically, the peak shift correction circuitry 61 adds a certain energy value to the energy of the photons detected by the photon-counting CT detection circuitry 41 such that a count value of the first counter 41c in the energy bin of the energy spectrum of the X-rays made incident on the X-ray detection element 31 falls within a predetermined range including a count value of the first counter 41c in an energy bin including the peak generated by the characteristic X-rays of a reference X-ray energy spectrum. The count value correction circuitry 62 performs correction after the correction performed by the peak shift correction circuitry 61.

Otherwise, the peak shift correction circuitry 61 adds a certain energy value to the energy of the photons detected by the photon-counting CT detection circuitry 41 such that the sum of squares, over the energy bins, of a difference in a count value output from the photon-counting CT detection circuitry 41 between an energy bin of a reference X-ray energy spectrum and an energy bin of an energy spectrum of the X-rays made incident on the X-ray detection element 31 has a minimum value. Specifically, the peak shift correction circuitry 61 adds a certain energy value to the energy of the photons detected by the photon-counting CT detection circuitry 41 such that the sum of squares, over the energy bins, of a difference in a count value of the first counter 41c between an energy bin of a reference X-ray energy spectrum and an energy bin of the energy spectrum of the X-rays made incident on the X-ray detection element 31 has a minimum value. The count value correction circuitry 62 performs correction after the correction performed by the peak shift correction circuitry 61. The details of the corrections performed by the peak shift correction circuitry 61 will be described later.

The count value correction circuitry 62 calculates count values for the respective energy bins in the case where the integral CT detection circuitry operates, from the integral value and the count values for the respective energy bins, and corrects the integral value based on the count values. Specifically, the count value correction circuitry 62 calculates the count values for the respective energy bins in the case where the integral CT detection circuitry 42 operates, from the count values of the second counter 42c and the count values for each of the energy bins obtained by the first counter 41c, to correct the count values of the second counter 42c based on the calculated count values. The details of the correction performed by the count value correction circuitry 62 will be described later.

The projection data generation circuitry 63 generates projection data based on the count values of the second counter 42c corrected by the count value correction circuitry 62.

The rotating frame 7 is an annular frame that supports the X-ray generator 22 and the X-ray detector 3 in a manner facing each other with the subject P interposed therebetween. The rotating frame 7 is driven by the gantry driver 213 and rotates in a circular path centered on the subject P at high velocities.

The couch apparatus 8 includes a couch drive device 81 and a couchtop 82. The couchtop 82 is a bed on which subject P is placed. The couch drive device 81, under the control of a scan controller 93 described later, moves the subject P in the rotating frame 7 by moving the couchtop 82, on which the subject P is placed, in the body axis direction. The gantry apparatus 2 performs a helical scan in which the subject P is scanned in a spiral manner by rotating the rotating frame 7 while moving the couchtop 82, for example. Alternatively, the gantry apparatus 2 performs a conventional scan in which the subject P is scanned in a circular path by rotating the rotating frame 7 while the position of the subject P is fixed after moving the couchtop 82. Alternatively, the gantry apparatus 2 performs a step-and-shoot method in which the conventional scan is performed at a plurality of scan areas by moving the position of the couchtop 82 at regular intervals.

The console apparatus 9 receives the operation of the photon-counting X-ray CT apparatus 1 by a user and performs a variety of image processing such as reconstruction processing of projection data collected by the gantry apparatus 2. The console apparatus 9 includes an input circuitry 91, a display 92, the scan controller 93, a preprocessing circuitry 94, a data storage circuitry 95, an image reconstruction circuitry 96, an image storage circuitry 97, and a controller 98.

The input circuitry 91 is a mouse, a keyboard, and others used by the user of the photon-counting X-ray CT apparatus 1 to input various instructions and various settings. The input circuitry 91 transfers the information on the instructions and settings received from the user to the controller 98. The display 92 is a monitor that is referred to by the user. The display 92 displays the results of a variety of image processing, and graphical user interfaces (GUIs) to receive various settings from the user via the input circuitry 91, for example.

The scan controller 93, under the control of the controller 98, controls the operations of the gantry controller 21, the data collection circuitry 5, the generation circuitry 6, and the couch drive device 81. Specifically, when photon-counting CT imaging and integral CT imaging are performed, by controlling the gantry controller 21, the scan controller 93 rotates the rotating frame 7, causes the X-ray tube 221 to emit X-rays, and adjusts the aperture and position of the collimator 223. Under the control of the controller 98, the scan controller 93 further controls the data collection circuitry 5. Under the control of the controller 98, by further controlling the couch drive device 81, the scan controller 93 moves the couchtop 82 at the time of imaging the subject P.

The preprocessing circuitry 94 performs correction processing on the projection data generated by the projection data generation circuitry 63. The correction processing is logarithmic conversion, offset correction, sensitivity correction, beam hardening correction, and scattered ray correction, for example. The preprocessing circuitry 94 stores the corrected projection data in the data storage circuitry 95. The projection data on which the correction processing has been performed by the preprocessing circuitry 94 is also referred to as raw data.

The data storage circuitry 95 stores therein the raw data, that is, the projection data on which the correction processing has been performed by the preprocessing circuitry 94. The image reconstruction circuitry 96 reconstructs the projection data stored in the data storage circuitry 95 and generates a reconstruction image. Various methods can be used as the reconstruction method. An example of the reconstruction method is back-projection processing. The back-projection processing includes a filtered back-projection (FBP) method, for example. The image reconstruction circuitry 96 may perform reconstruction processing using an iterative approximation method, for example. The image storage circuitry 97 stores therein the reconstruction image generated by the image reconstruction circuitry 96.

Each of the data storage circuitry 95 and the image storage circuitry 97 in the foregoing can be implemented with a random access memory (RAM), a semiconductor memory device such as a flash memory, a hard disk, or an optical disk, for example. The scan controller 93, the preprocessing circuitry 94, the image reconstruction circuitry 96, and the controller 98 in the foregoing can be implemented with an integrated circuit such as an application specific integrated circuit (ASIC) and a field programmable gate array (FPGA), or an electronic circuit such as a central processing unit (CPU) and a micro processing unit (MPU).

The controller 98 controls the photon-counting X-ray CT apparatus 1 by controlling the operations of the gantry apparatus 2, the couch apparatus 8, and the console apparatus 9. The controller 98 controls the scan controller 93 to perform scan and collects projection data from the gantry apparatus 2. The controller 98 controls the preprocessing circuitry 94 to perform the above-described correction processing on the projection data. The controller 98 executes control such that the projection data stored in the data storage circuitry 95 and the image data stored in the image storage circuitry 97 are displayed on the display 92.

Figure 4:
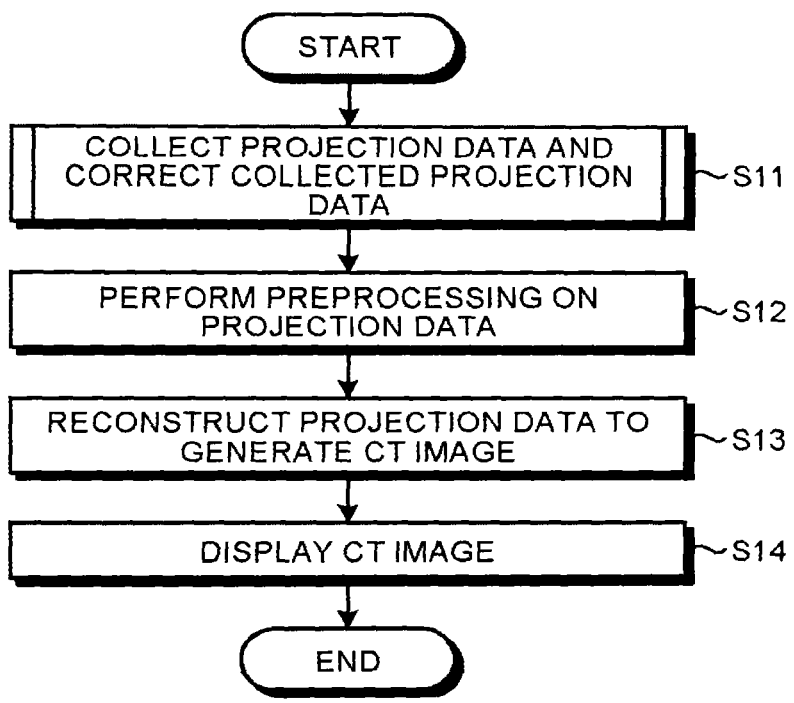
FIG. 4 is a flowchart illustrating an example of processing performed by the photon-counting X-ray CT apparatus according to the first embodiment.

Next, with reference to FIG. 4 to FIG. 12, one example of processing performed by the photon-counting X-ray CT apparatus 1 in the first embodiment will be described. FIG. 4 is a flowchart illustrating one example of processing performed by the photon-counting X-ray CT apparatus 1 in the first embodiment.

As illustrated in FIG. 4, the controller 98 collects projection data, and corrects the collected projection data (Step S11). Specifically, the controller 98 controls the gantry apparatus 2, the couch apparatus 8, and the console apparatus 9 to perform photon-counting CT imaging and integral CT imaging. Thereafter, the controller 98 controls the data collection circuitry 5 to collect projection data. The controller 98 controls the generation circuitry 6 to correct the projection data collected by the data collection circuitry 5. The details of Step S11 will be described later.

The controller 98 controls the preprocessing circuitry 94 to perform the above-described correction processing on the projection data (Step S12). The corrected projection data is stored in the data storage circuitry 95. The controller 98 controls the image reconstruction circuitry 96 to reconstruct the projection data stored in the data storage circuitry 95 and generate a CT image (Step S13). The generated CT image is stored in the image storage circuitry 97. The controller 98 controls the display 92 to display the CT image stored in the image storage circuitry 97 (Step S14).

Figure 5:
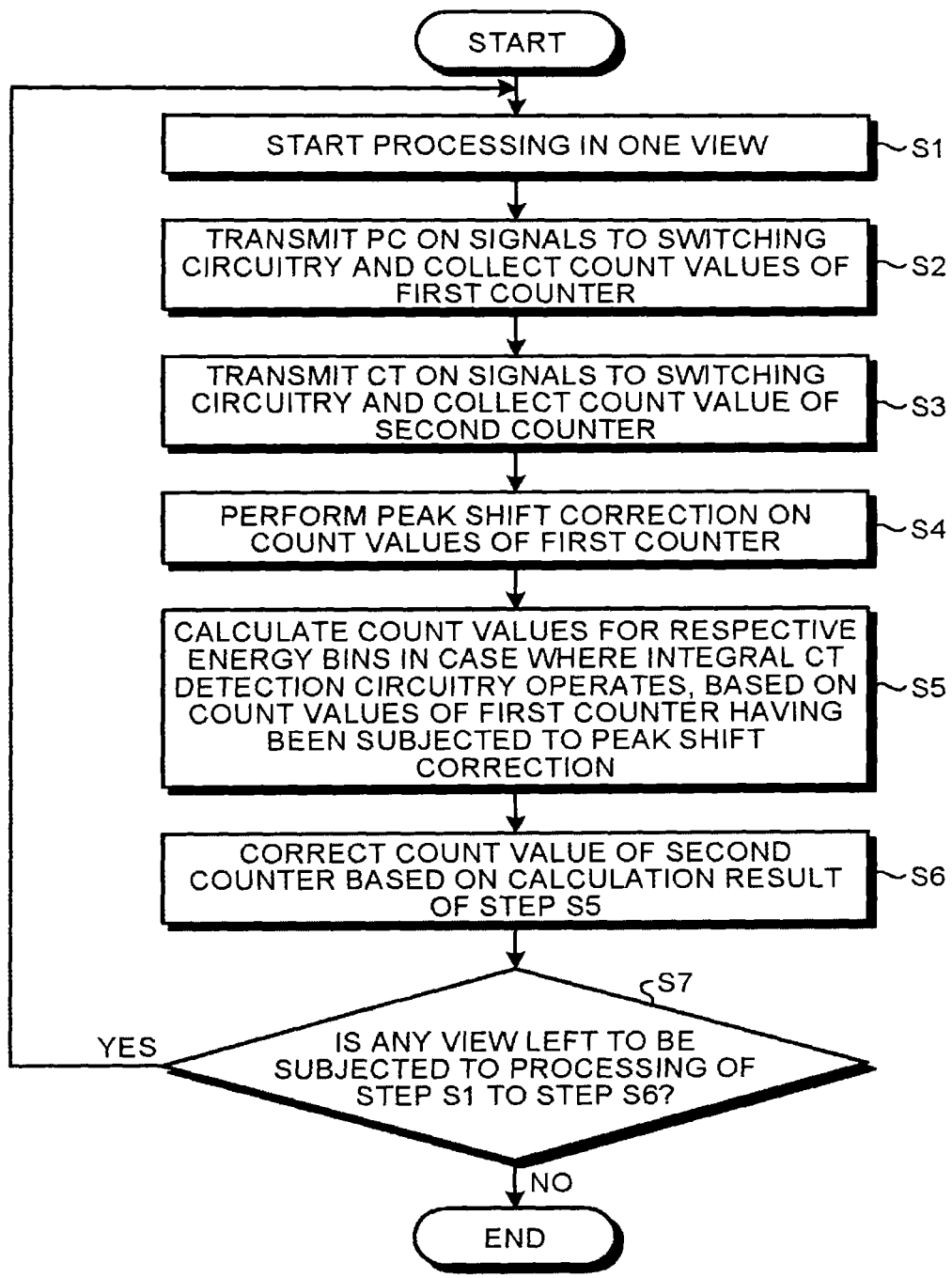
FIG. 5 is a flowchart illustrating an example of processing performed at Step S11 in FIG. 4 in the first embodiment.
Figure 6:
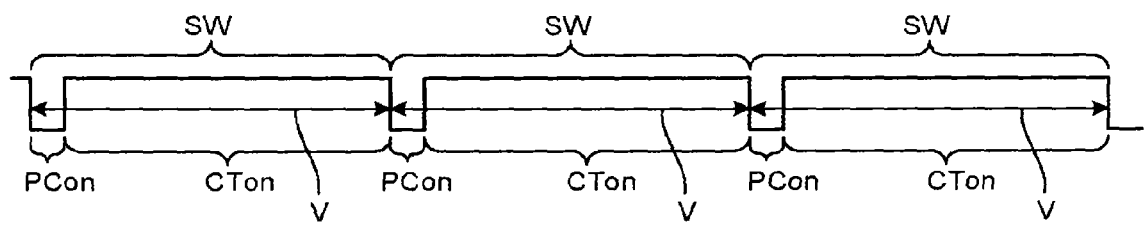
FIG. 6 is a diagram illustrating an example of switching signals that is transmitted by control circuitry according to the first embodiment to switching circuitry.
Figure 7:
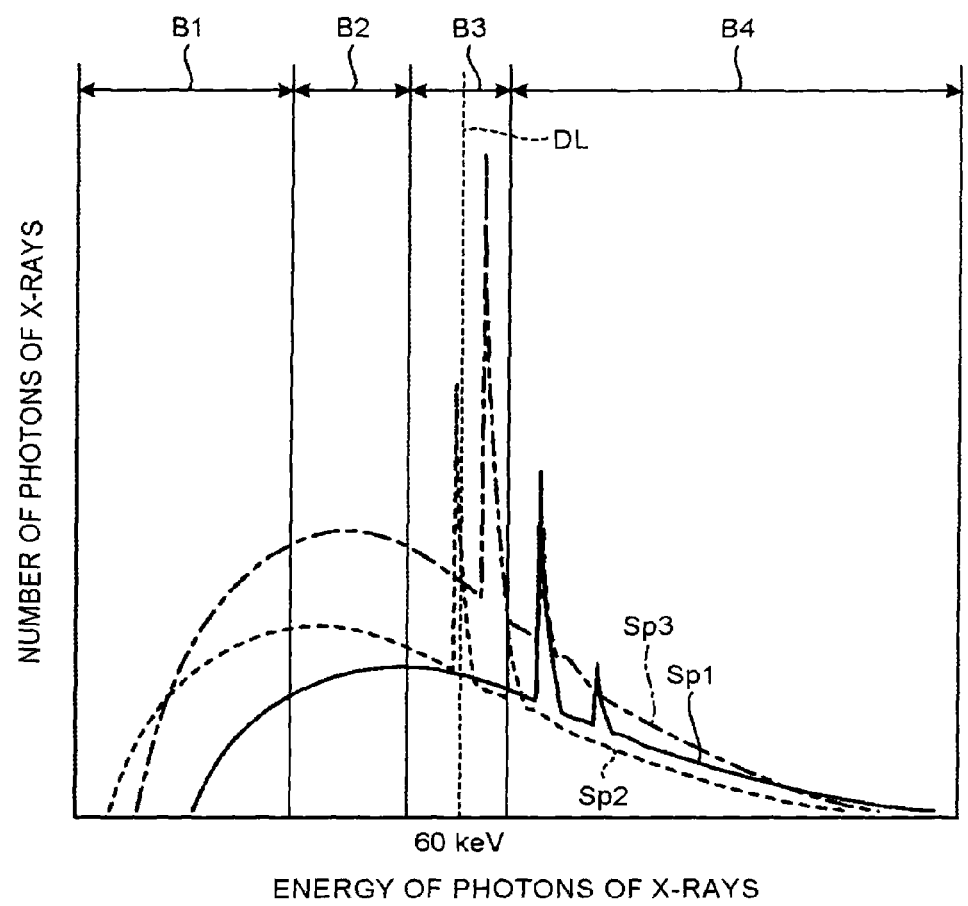
FIG. 7 is a diagram illustrating energy spectrums of X-rays before peak shift correction is performed.
Figure 8:
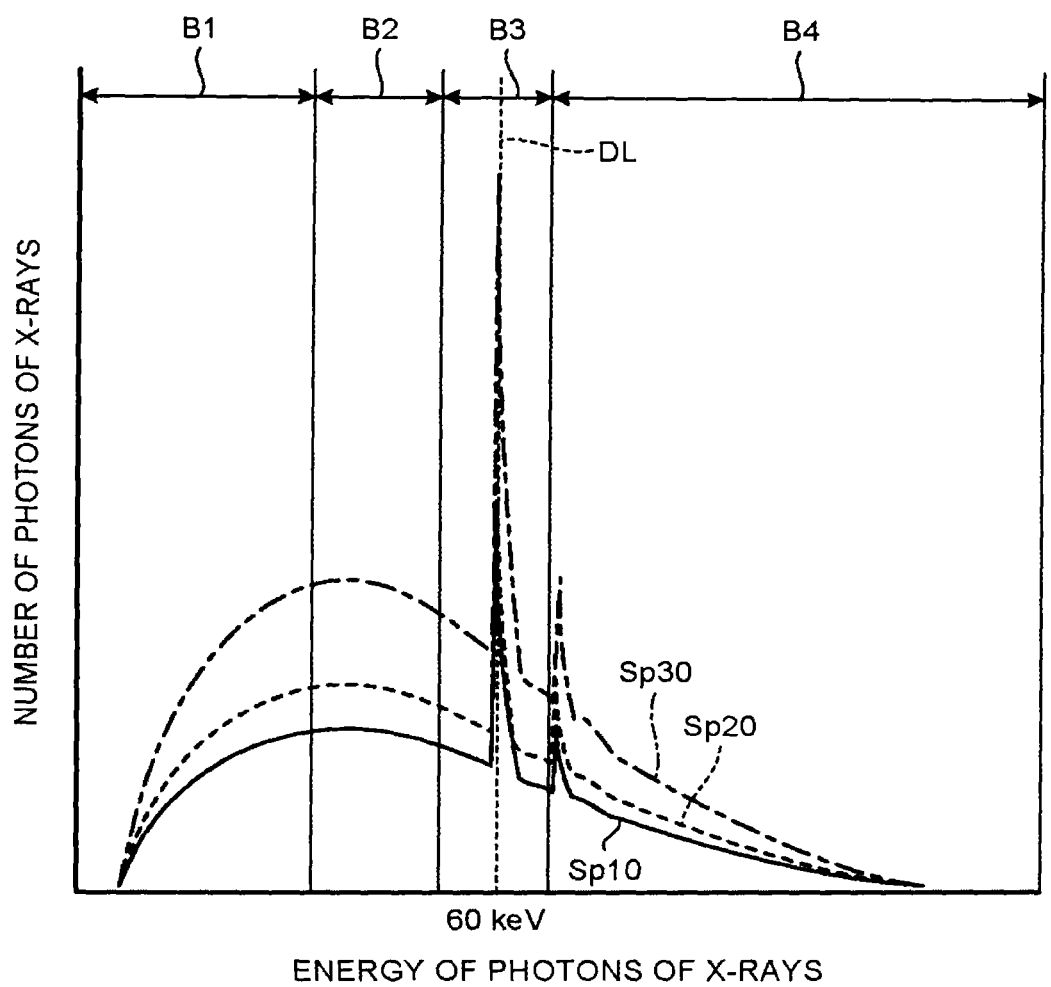
FIG. 8 is a diagram illustrating energy spectrums of X-rays after peak shift correction is performed.
Figure 9:
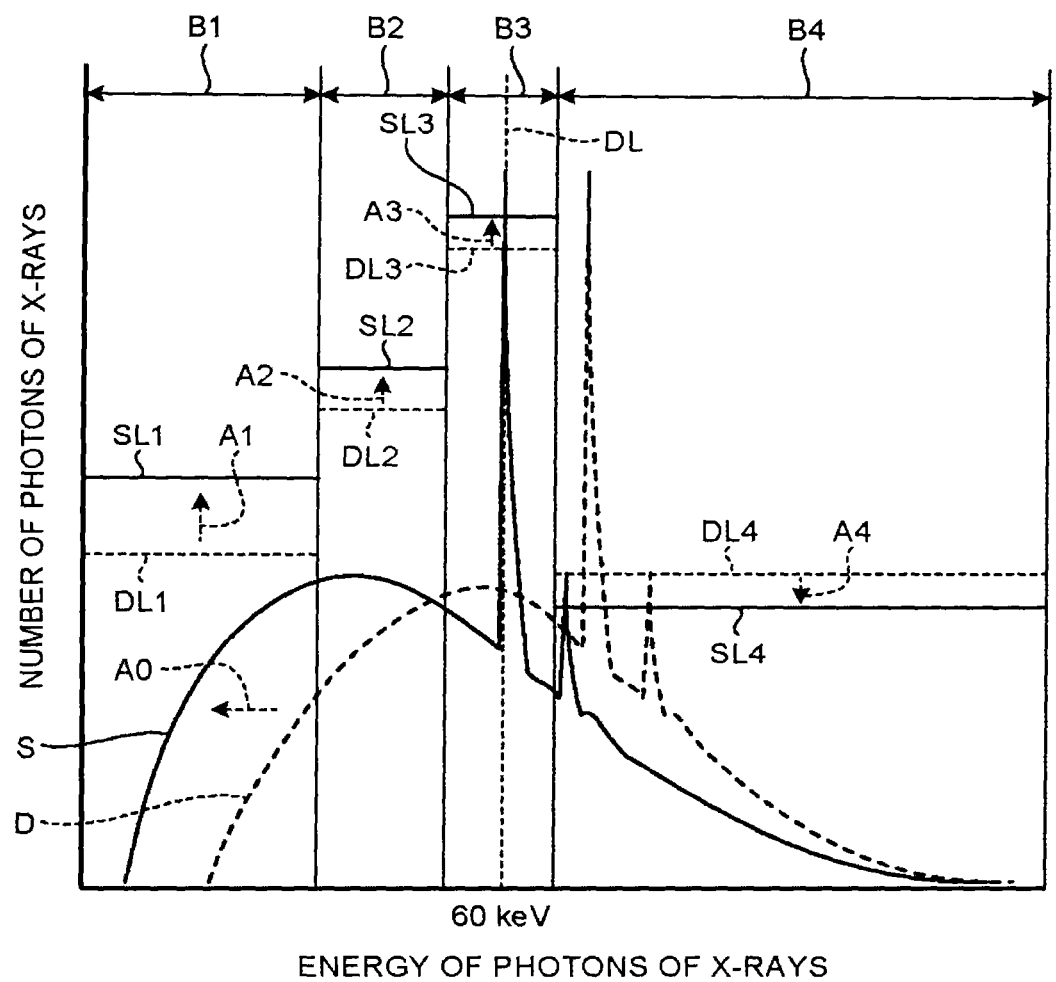
FIG. 9 is a diagram for explaining peak shift correction.
Figure 10:
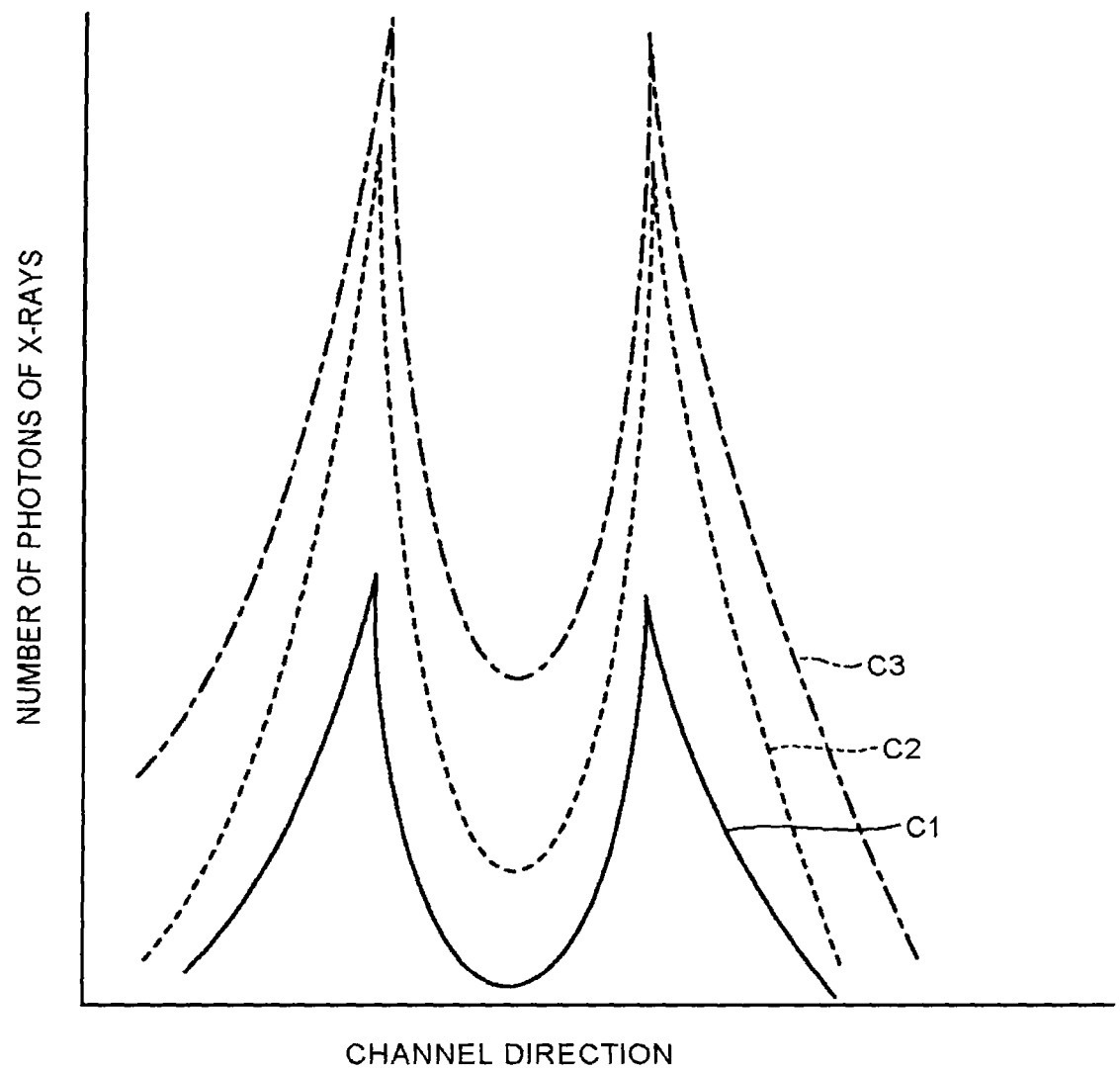
FIG. 10 is a diagram illustrating count values of a second counter before count value correction is performed.
Figure 11:
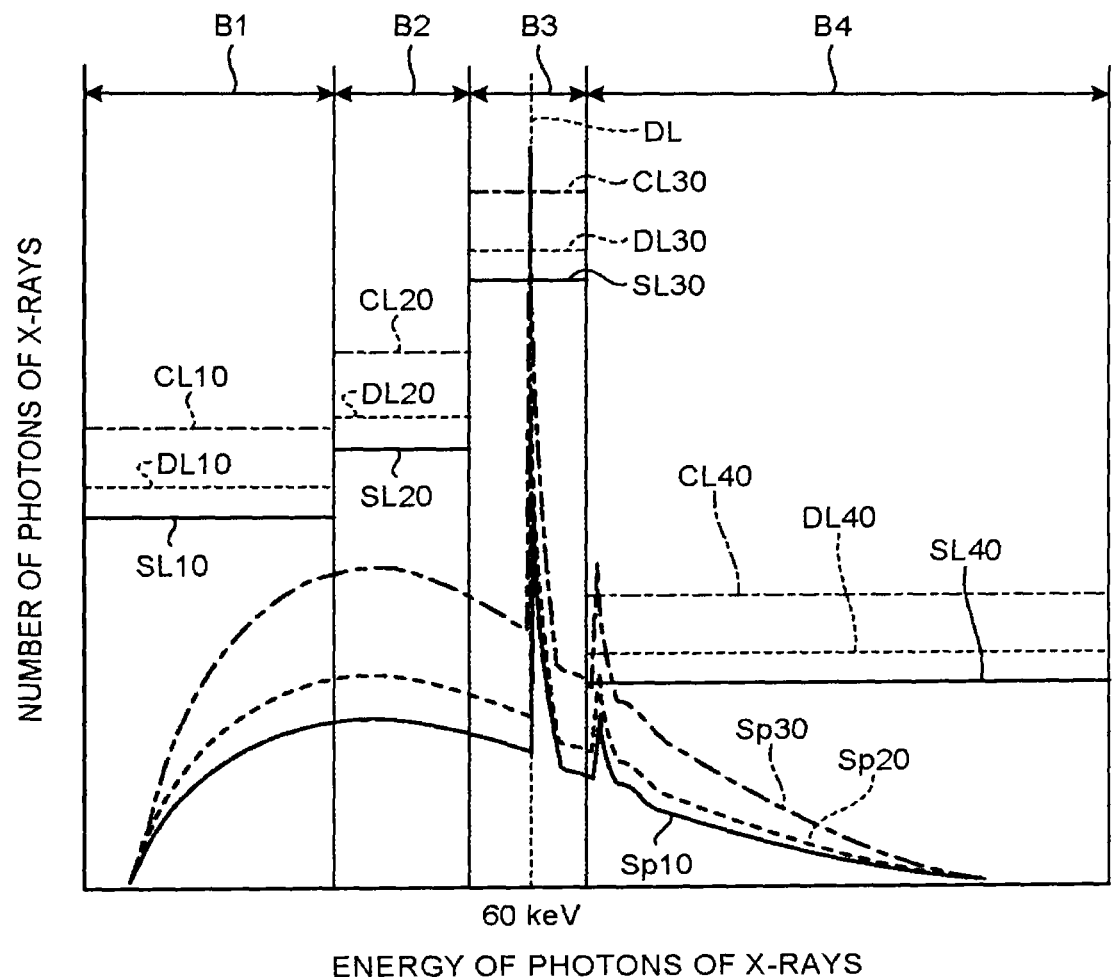
FIG. 11 is a diagram illustrating energy spectrums of X-rays made incident on different X-ray detection elements and count values corresponding thereto and counted by a first counter.
Figure 12:
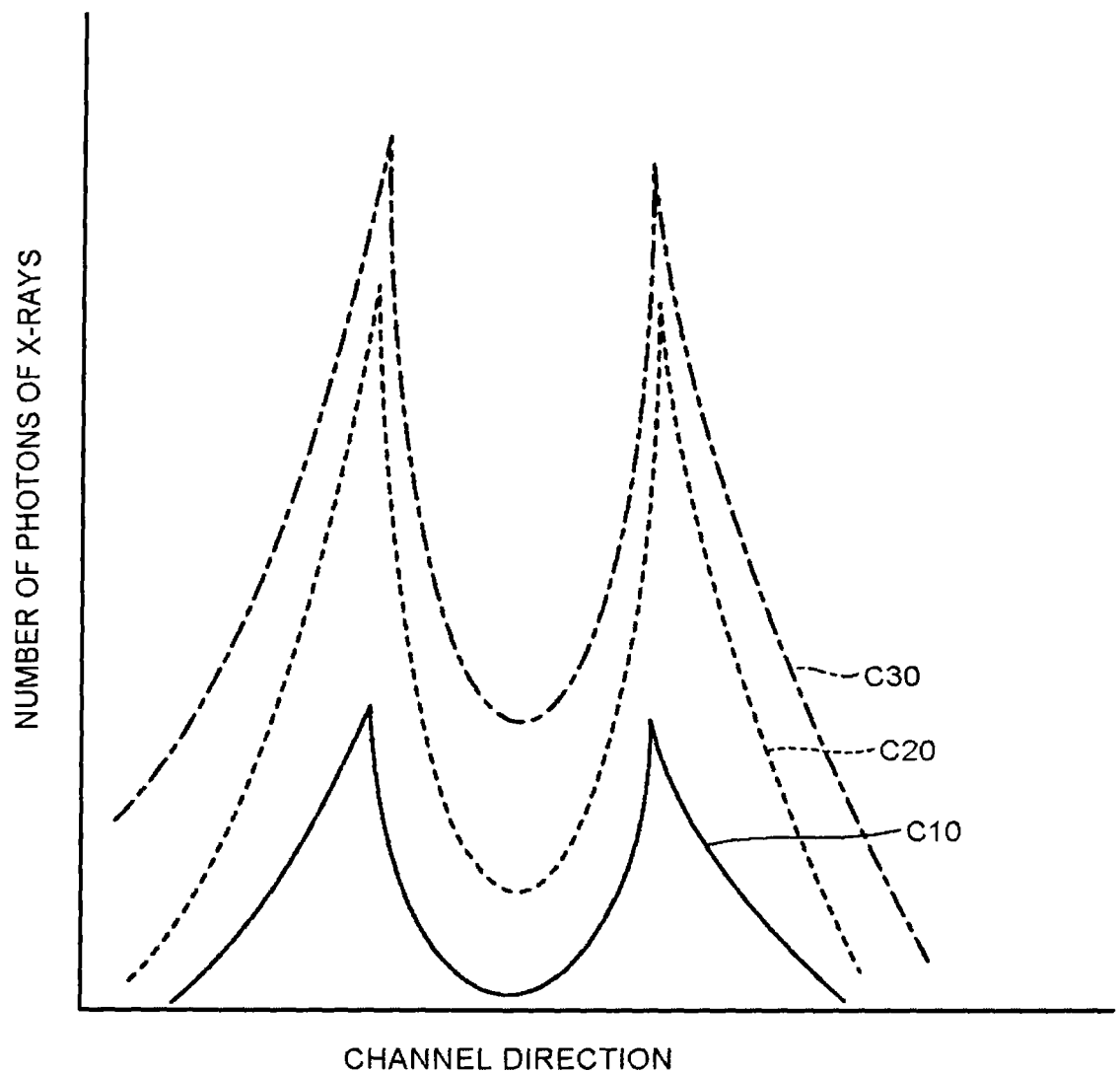
FIG. 12 is a diagram illustrating count values of the second counter after count value correction is performed.

The following is explanation of the details of Step S11 in FIG. 4 with reference to FIG. 5 to FIG. 12. FIG. 5 is a flowchart illustrating an example of processing performed at Step S11 of FIG. 4 in the first embodiment. FIG. 6 is a diagram illustrating an example of switching signals SW that is transmitted by the control circuitry 51 according to the first embodiment to the switching circuitry 40. FIG. 7 is a diagram illustrating energy spectrums of X-rays before peak shift correction is performed. FIG. 8 is a diagram illustrating the energy spectrums of X-rays after peak shift correction is performed. FIG. 9 is a diagram for explaining peak shift correction. FIG. 10 is a diagram illustrating count values of the second counter before count value correction is performed. FIG. 11 is a diagram illustrating energy spectrums of the X-rays made incident on different X-ray detection elements 31 and count values corresponding thereto and counted by the first counter. FIG. 12 is a diagram illustrating count values of the second counter after count value correction is performed.

As illustrated in FIG. 5, the scan controller 93 starts processing in one view (Step S1). First, as illustrated in FIG. 6, the control circuitry 51 transmits PC ON signals to the switching circuitry 40 included in the detection circuitry 4, to collect the count values of the first counter 41c (Step S2). Next, as illustrated in FIG. 6, the control circuitry 51 transmits CT ON signals to the switching circuitry 40 included in the detection circuitry 4, to collect the count value of the second counter 42c (Step S3).

As illustrated in FIG. 6, in each view V, the period for which the photon-counting CT ON signal PCon is transmitted is shorter than the period for which the integral CT ON signal CTon is transmitted. This is because, in photon-counting CT, "pile up" occurs, in the case where the X-rays made incident on the X-ray detection element 31 have high dose. "Pile up" is a phenomenon in which a plurality of electric charges generated by individual photons of the X-rays are erroneously counted as one electric charge. In addition, the number of photons of the X-rays made incident on the X-ray detection elements 31 varies according to the setting of the X-ray generator 22 and the size of the subject. For this reason, the control circuitry 51 preferably shortens the period for which the photon-counting CT ON signal PCon is transmitted, when the number of photons of the X-rays made incident on the X-ray detection element 31 increases.

The peak shift correction circuitry 61 performs peak shift correction on the count values of the first counter 41c (Step S4). FIG. 7 illustrates an energy spectrum Sp1, an energy spectrum Sp2, and an energy spectrum Sp3 in the X-ray detection elements 31 with different X-rays irradiated from the X-ray tube 221 using tungsten as a target, and a dot line DL indicating 60 keV serving as the peak position of Kα line of tungsten. Because FIG. 7 illustrates the state before peak shift correction is performed, the peaks of the characteristic X-rays of the energy spectrum Sp1, the energy spectrum Sp2, and the energy spectrum Sp3 illustrated in FIG. 7 do not agree with the dot line DL. This is because the energies detected by the respective detection circuitry 4 vary due to variations in the feedback capacitances 43 included in the respective detection circuitry 4, even when the photons of the X-rays have the same energy. For this reason, the count values of the first counter 41c corresponding to the energy spectrum Sp1, the energy spectrum Sp2, and the energy spectrum Sp3 are deviated.

FIG. 8 illustrates an energy spectrum Sp10, an energy spectrum Sp20, and an energy spectrum Sp30 that are obtained by performing peak shift correction on the energy spectrum Sp1, the energy spectrum Sp2, and the energy spectrum Sp3 illustrated in FIG. 7, and a dot line DL indicating 60 keV serving as the peak position of Kα line of tungsten. Because FIG. 8 illustrates the state after peak shift correction is performed, the peaks of the characteristic X-rays of the energy spectrum Sp10, the energy spectrum Sp20, and the energy spectrum Sp30 illustrated in FIG. 8 agree with the dot line DL. For this reason, the count values of the first counter 41c corresponding to the energy spectrum Sp1, the energy spectrum Sp2, and the energy spectrum Sp3 are not deviated.

In photon-counting CT, the count values that are actually obtained are count values of photons for respective energy bins that are set on each of the energy spectrums of the X-rays. The energy spectrum Sp1, the energy spectrum Sp2, and the energy spectrum Sp3 illustrated in FIG. 7 and the energy spectrum Sp10, the energy spectrum Sp20, and the energy spectrum Sp30 illustrated in FIG. 8 are illustrated conceptually.

Next, the details of peak shift correction will be explained hereinafter with reference to FIG. 9. FIG. 9 illustrates a first energy bin B1, a second energy bin B2, a third energy bin B3, and a fourth energy bin B4, an energy spectrum S and an energy spectrum D of X-rays that are made incident on different X-ray detection elements 31 in one view, and a dot line DL indicating the peak position of Kα line of tungsten.

The shape of the energy spectrum S is different from the shape of the energy spectrum D. This is because the X-rays made incident on the different X-ray detection elements 31 have transmitted different types of materials and have different path lengths from the X-ray tube 221 to the respective X-ray detection elements 31. FIG. 9 conceptually illustrates the energy spectrum S and the energy spectrum D for explaining peak shift correction.

As described above, in photon-counting CT, the count values that are actually obtained are count values of photons for respective energy bins that are set on each of the energy spectrums of the X-rays. For this reason, the count values obtained by the first counter 41c for the energy spectrum S are indicated by a line segment SL1 in the first energy bin B1, a line segment SL2 in the second energy bin B2, a line segment SL3 in the third energy bin B3, and a line segment SL4 in the fourth energy bin B4. The count values obtained by the first counter 41c for the energy spectrum D are indicated by a line segment DL1 in the first energy bin B1, a line segment DL2 in the second energy bin B2, a line segment DL3 in the third energy bin B3, and a line segment DL4 in the fourth energy bin B4.

As illustrated in FIG. 9, the third energy bin B3 is an energy bin including the dot line DL indicating 60 keV serving as the peak position of the Kα line of tungsten, and has the smallest width among the four energy bins. When the width of the third energy bin B3 is set small like this, because the count value of the first counter 41c greatly varies according to whether the peak of the characteristic X-rays is included therein, the peak position of the characteristic X-rays can be specified to a certain degree from the count value of the first counter 41c. In FIG. 9, the peak of the characteristic X-rays of the energy spectrum S is included in the third energy bin B3, and the peak of the characteristic X-rays of the energy spectrum D is not included in the third energy bin B3. For this reason, as illustrated with the line segment SL and the line segment DL3 in FIG. 9, the count value of the first counter 41c for the energy spectrum S in the third energy bin B3 is larger than that of the energy spectrum D in the third energy bin B3.

Suppose that the peak shift correction circuitry 61 moves the energy spectrum D in parallel in the direction of the arrow A0 such that the peak of the characteristic X-rays of the energy spectrum D falls within the third energy bin B3. This correction corresponds to addition of a certain energy value by the peak shift correction circuitry 61 to the energy of the photons detected by the photon-counting CT detection circuitry 41. The energy value to be added is a positive value or a negative value. In such a case, the count values of the first counter 41c for the X-rays having the energy spectrum D change as follows. The count values obtained by the first counter 41c increase in the first energy bin B1, the second energy B2, and the third energy B3, because the area enclosed by the energy spectrum D increases in each of the energy bins. Specifically, the line segment DL1 in the first energy bin B1, the line segment DL2 in the second energy bin B2, and the line segment DL3 in the third energy bin B3 are moved in the respective directions indicated by an arrow A1, an arrow A2, and an arrow A3, respectively. The count value obtained by the first counter 41c decreases in the fourth energy bin B4, because the area enclosed by the energy spectrum D decreases in the fourth energy bin B4. Specifically, the line segment DL4 in the fourth energy bin B4 is moved in the direction indicated by an arrow A4.

Specifically, the peak shift correction circuitry 61 reduces deviation of the count value of the first counter 41c in the energy bin including the peak of the characteristic X-rays, by moving the energy spectrum D in parallel in the energy direction. For example, the peak shift correction circuitry 61 moves the energy spectrum D in parallel in the energy direction such that the count value of the first counter 41c for the energy spectrum D in the third energy bin B3 agrees with the count value of the first counter 41c for the energy spectrum S in the third energy bin B3. Otherwise, for example, the peak shift correction circuitry 61 may move the energy spectrum D in parallel in the energy direction such that the count value of the first counter 41c for the energy spectrum D in the third energy bin B3 falls within a predetermined range including the count value of the first counter 41c for the energy spectrum S in the third energy bin B3.

In addition, when the numbers of photons in all the energy bins of the energy spectrum D are a fixed number of times as high as the values illustrated in FIG. 9, the peak shift correction circuitry 61 should move the energy spectrum D in parallel in the energy direction such that the sum of squares of the difference in the count value of the first counter 41c in each energy bin has a minimum value.

Although the explanation described above illustrates the case where the peak of the characteristic X-rays of the energy spectrum S agrees with the dot line DL indicating 60 keV serving as the peak position of the Kα line of tungsten, it suffices that at least the whole peak of the characteristic X-rays of the energy spectrum S is included in the third energy bin B3. The peak shift correction circuitry 61 can perform the correction described above, with a prepared count value of the first counter 41c for the reference X-ray energy spectrum, that is, the energy spectrum S with which the whole peak of the characteristic X-rays is included in the third energy bin B3.

The count value correction circuitry 62 calculates the count values for the respective energy bins in the case where the integral CT detection circuitry 42 operates, based on the count values of the first counter 41c having been subjected to peak shift correction (Step 35). The following is the details of the calculating method.

The following expression (1) is established, when the count value of the first energy bin B1 obtained by the first counter 41c is np (B1), the count value of the second energy bin B2 obtained by the first counter 41c is np (B2), the count value of the third energy bin B3 obtained by the first counter 41c is np (B3), the count value of the fourth energy bin B4 obtained by the first counter 41c is np (B4), and the total of the count values from the first energy bin B1 to the fourth energy bin B4 is np.

$$n_p = n_{p(B1)} + n_{p(B2)} + n_{p(B3)} + n_{p(B4)} \quad (1)$$

The following expression (2) is established, in the case where the integral CT detection circuitry 42 operates, when the count value of the first energy bin B1 is Np (B1), the count value of the second energy bin B2 is Np (B2), the count value of the third energy bin B3 is Np (B3), the count value of the fourth energy bin B4 is Np (B4), and the total of the count values from the first energy bin B1 to the fourth energy bin B4 is Np.

$$N_p = N_{p(B1)} + N_{p(B2)} + N_{p(B3)} + N_{p(B4)} \quad (2)$$

The following expression (3) is established with respect to the relation among the total np of the count values from the first energy B1 to the fourth energy bin B4, the total Np of the count values from the first energy 81 to the fourth energy bin B4, the count value np (Bk) of the kth energy bin Bk obtained by the first counter 41c, and the count value Np (Bk) (k=1, 2, 3, 4) of the kth energy bin Bk in the case where the integral CT detection circuitry 42 operates. With the expression (3), the count value correction circuitry 62 can calculate the count values for the respective energy bins in the case where the integral CT detection circuitry 42 operates, based on the count values of the first counter 41c having been subjected to peak shift correction.

$$N_{p(Bk)} = N_p * n_{p(Bk)} / n_p \quad (k=1, 2, 3, 4) \tag{3}$$

The count value correction circuitry 62 corrects the count value of the second counter 42c, based on the calculation result of Step S5 (Step S6). Specifically, the count value correction circuitry 62 subtracts the count value of the energy bin including much noise in the case where the integral CT detection circuitry 42 operates from the count value Np of the second counter 42c, based on the calculation result of Step S5. The following explanation illustrates the case where noise occurs in the first energy bin B1 due to scattered rays.

To remove influence of noise occurring in the first energy bin B1 due to scattered rays, the count value Np (B1) of the first energy bin B1 in the case where the integral CT detection circuitry 42 operates should be subtracted from the count value Np of the second counter 42c. The following expression (4) is established, when Np' is a value obtained by subtracting the count value Np (B1) of the first energy bin B1 in the case where the integral CT detection circuitry 42 operates from the count value Np of the second counter 42c.

$$N_p' = N_p - N_{p(B1)} \tag{4}$$

The following expression (5) can be derived from the expression (3) and the expression (4). The expression (5) indicates that the value Np' obtained by subtracting the count value Np (B1) of the first energy bin B1 in the case where the integral CT detection circuitry 42 operates from the count value Np of the second counter 42c can be calculated from the count value Np of the second counter 42c, the count value np (B1) of the first energy bin, the count value np (B2) of the second energy bin, the count value np (B3) of the third energy bin, and the count value np (B4) of the fourth energy bin that are obtained by the first counter 41c.

$$\begin{aligned} N_p' &= N_{p(B2)} + N_{p(B3)} + N_{p(B4)} \\ &= N_p * (n_{p(B2)} + n_{p(B3)} + n_{p(B4)})/n_p \\ &= N_p * (n_p - n_{p(B1)})/n_p \end{aligned} \tag{5}$$

The count value correction circuitry 62 corrects the count values of the second counter 42c with the following procedure using the expression (5). FIG. 10 illustrates a curve C1, a curve C2, and a curve C3. The curve C1, the curve C2, and the curve C3 indicate distributions of the count values of the second counter 42c before correction along the channel direction of the count values in different slice directions. The curve C1, the curve C2, and the curve C3 include noise caused by scattered rays as described above.

The count value correction circuitry 62 calculates the value Np' obtained by subtracting the count value Np (B1) of the first energy bin B1 in the case where the integral CT detection circuitry 42 operates from the count value Np of the second counter 42c, using the count values of the first counter 41c illustrated in FIG. 11 and the expression (5). As illustrated in FIG. 11, the count values of the first counter 41c in the respective energy bins of the energy spectrum Sp10 are indicated with a line segment SL10, a line segment SL20, a line segment SL30, and a line segment SL40. The count values of the first counter 41c in the respective energy bins of the energy spectrum Sp20 are indicated with a line segment DL10, a line segment DL 20, a line segment DL 30, and a line segment DL40. The count values of the first counter 41c in the respective energy bins of the energy spectrum Sp30 are indicated with a line segment CL10, a line segment CL 20, a line segment CL 30, and a line segment CL40.

FIG. 12 illustrates distributions of the calculated Np' along the channel direction, in different slice directions. A curve C10, a curve C20, and a curve C30 illustrated in FIG. 12 do not include noise caused by scattered rays described above.

The explanation described above illustrates the case of subtracting the count value Np (B1) in the first energy bin B1 in which noise caused by scattered rays occurs in the case where the integral CT detection circuitry 42 operates, but the correction performed by the count value correction circuitry 62 is not limited thereto. For example, when any metal exists in the region where photon-counting CT imaging and integral CT imaging are performed, the count value correction circuitry 62 may subtract the count value in the energy bin including the peak of the metal in the case where the integral CT detection circuitry 42 operates from the count value Np of the second counter 42c. In this manner, the photon-counting X-ray CT apparatus 1 reduces metal artifacts. Otherwise, the count value correction circuitry 62 may subtract the count value in the energy bin in which influence of noise strongly occurs in the case where the integral CT detection circuitry 42 operates from the count value Np of the second counter 42c.

The scan controller 93 determines whether any view on which the processing of Step S1 to Step S6 is to be performed is left (Step S7). When the scan controller 93 determines that any view on which the processing of Step S1 to Step S6 is to be performed is left (Yes of Step S7), the processing returns to Step S1. When the scan controller 93 determines that no view on which the processing of Step S1 to Step S6 is to be performed is left (No of Step S7), the processing is finished.

Figure 13:
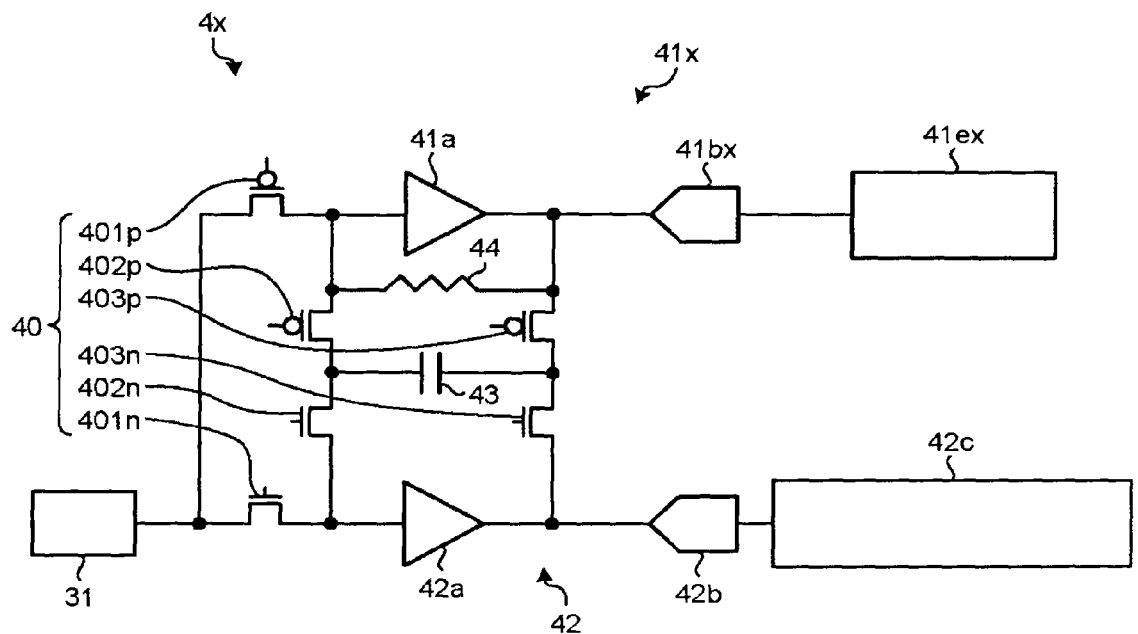
FIG. 13 is a diagram illustrating another example of the detection circuitry according to the first embodiment.

The photon-counting X-ray CT apparatus 1 may include detection circuitry 4x illustrated in FIG. 13, instead of the detection circuitry 4 illustrated in FIG. 3. The detection circuitry 4x includes photon-counting CT detection circuitry 41x. The photon-counting CT detection circuitry 41x includes an A/D converter 41bx and arithmetic circuitry 41ex. The operation and the other structures of the detection circuitry 4x are the same as those of the detection circuitry 4 described above, and explanation thereof is omitted.

The A/D converter 41bx converts the voltage pulses received from the first amplifier 41a into digital electrical signals and outputs the digital electrical signals. The arithmetic circuitry 41ex is circuitry having a function corresponding to the comparator 411, the comparator 412, and the comparator 413 described above, and a function corresponding to the first counter 41c. The arithmetic circuitry 41ex distributes the electrical signals that are output from the A/D converter 41bx to any of the energy bins set on the energy spectrum of the X-rays, by the function corresponding to the comparator 411, the comparator 412, and the comparator 413 described above. The arithmetic circuitry 41ex counts the electrical signals for each of the energy bins set on the energy spectrum of the X-rays, by the function corresponding to the first counter 41c.

Figure 14:
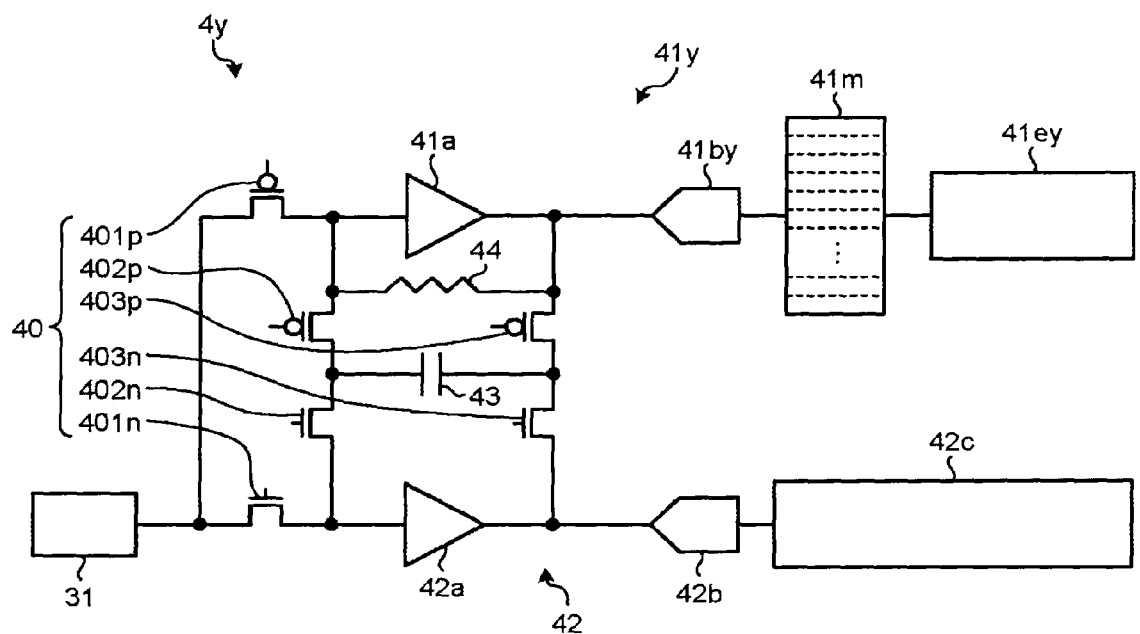
FIG. 14 is a diagram illustrating another example of the detection circuitry according to the first embodiment.

Otherwise, the photon-counting X-ray CT apparatus 1 may include detection circuitry 4y illustrated in FIG. 14, instead of the detection circuitry 4 illustrated in FIG. 3. The detection circuitry 4y includes photon-counting CT detection circuitry 41y. The photon-counting CT detection circuitry 41y includes an A/D converter 41by, a memory 41m, and arithmetic circuitry 41ey. The operation and the other structures of the detection circuitry 4y are the same as those of the detection circuitry 4 described above, and explanation thereof is omitted.

The A/D converter 41by converts the voltage pulses received from the first amplifier 41a into digital electrical signals and outputs the digital electrical signals. The memory 41m is, for example, a memory having a double buffer structure that repeats writing, reset, and swap. The memory 41m stores electrical signals that are output from the A/D converter 41by per unit time as, for example, a pulse string of 10 bits, and outputs the pulse string to the arithmetic circuitry 41ey. The arithmetic circuitry 41ey distributes the pulse strings that are output from the memory 41m to any of the energy bins set on the energy spectrum of the X-rays, by the function corresponding to the comparator 411, the comparator 412, and the comparator 413 described above. The arithmetic circuitry 41ey counts the pulse strings for each of the energy bins set on the energy spectrum of the X-rays, by the function corresponding to the first counter 41c.

Figure 15:
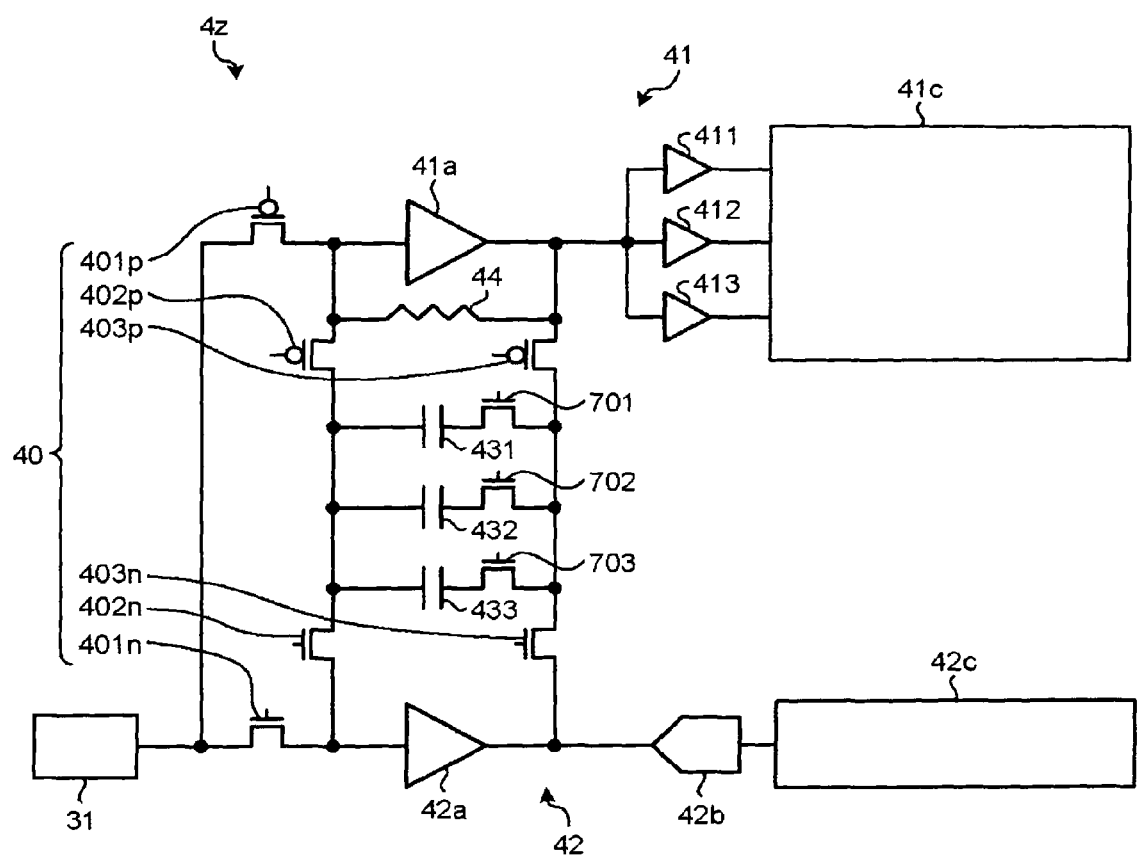
FIG. 15 is a diagram illustrating another example of the detection circuitry according to the first embodiment.

Otherwise, the photon-counting X-ray CT apparatus 1 may include detection circuitry 4z illustrated in FIG. 15, instead of the detection circuitry 4 illustrated in FIG. 3. The detection circuitry 4z includes a plurality of feedback capacitances that are connected with the photon-counting CT detection circuitry 41 and the integral CT detection circuitry 42 in parallel. The feedback capacitance used for outputting voltage pulses is switched according to the magnitude of the electric charges output from the X-ray detection element 31.

The detection circuitry 4z includes a feedback capacitance 431, a feedback capacitance 432, a feedback capacitance 433, an n-type MOSFET 701, an n-type MOSFET 702, and an n-type MOSFET 703, instead of the feedback capacitance 43 illustrated in FIG. 3.

The terminal of the feedback capacitance 431 on the X-ray detection element 31 side is connected with the terminal of the resistor 44 on the X-ray detection element 31 side via the p-type MOSFET 402p. The terminal of the feedback capacitance 431 on the first counter 41c side is connected with the terminal of the resistor 44 on the first counter 41c side via the p-type MOSFET 403p. Specifically, the feedback capacitance 431 is connected with the resistor 44 and the first amplifier 41a in parallel. An n-type MOEFET 701 is installed between the terminal of the feedback capacitance 431 on the first counter 41c side and the p-type MOSFET 403p.

The terminal of the feedback capacitance 432 on the X-ray detection element 31 side is connected with the terminal of the resistor 44 on the X-ray detection element 31 side via the p-type MOSFET 402p. The terminal of the feedback capacitance 432 on the first counter 41c side is connected with the terminal of the resistor 44 on the first counter 41c side via the p-type MOSFET 403p. Specifically, the feedback capacitance 432 is connected with the resistor 44 and the first amplifier 41a in parallel. An n-type MOEFET 702 is installed between the terminal of the feedback capacitance 432 on the first counter 41c side and the p-type MOSFET 403p.

The terminal of the feedback capacitance 433 on the X-ray detection element 31 side is connected with the terminal of the resistor 44 on the X-ray detection element 31 side via the p-type MOSFET 402p. The terminal of the feedback capacitance 433 on the first counter 41c side is connected with the terminal of the resistor 44 on the first counter 41c side via the p-type MOSFET 403p. Specifically, the feedback capacitance 433 is connected with the resistor 44 and the first amplifier 41a in parallel. An n-type MOEFET 703 is installed between the terminal of the feedback capacitance 433 on the first counter 41c side and the p-type MOSFET 403p.

Switching of each of the n-type MOSFET 701, the n-type MOSFET 702, and the n-type MOSFET 703 between the conductive state and the non-conductive state is independent of switching of the MOSFETs included in the switching circuitry 40 described above between the conductive state and the non-conductive state. Specifically, a signal other than the switching signal described above switches each of the n-type MOSFET 701, the n-type MOSFET 702, and the n-type MOSFET 703 between the conductive state and the non-conductive state. Switches of the n-type MOSFET 701, the n-type MOSFET 702, and the n-type MOSFET 703 between the conductive state and the non-conductive state are mutually independent.

Each of the n-type MOSFET 701, the n-type MOSFET 702, and the n-type MOSFET 703 is switched between the conductive state and the non-conductive state, in accordance with the magnitude of the electric charges output from the X-ray detection element 31. The magnitude of the electric charges output from the X-ray detection element 31 correlates with the magnitude of the voltage amplified by the first amplifier 41a.

For example, when large electric charges are output from the X-ray detection element 31, the n-type MOSFET 701, the n-type MOSFET 702, and the n-type MOSFET 703 are switched to the conductive state. In this manner, the feedback capacitance 431, the feedback capacitance 432, and the feedback capacitance 433 operate as one feedback capacitance, and can output voltage pulses corresponding to the electric charges output from the X-ray detection element 31, without being saturated. With this structure, the photon-counting CT detection circuitry 41 can output accurate count values for the respective energy bins, based on the voltage pulses output from the feedback capacitance 431, the feedback capacitance 432, and the feedback capacitance 433 that operate as one feedback capacitance.

By contrast, when small electric charges are output from the X-ray detection element 31, the n-type MOSFET 701, the n-type MOSFET 702, or the n-type MOSFET 703 is switched to the conductive state. In this manner, the feedback capacitance 431, the feedback capacitance 432, or the feedback capacitance 433 can output voltage pulses corresponding to the electric charges output from the X-ray detection element 31, without being saturated. Otherwise, the n-type MOSFET 701, the n-type MOSFET 702, or the n-type MOSFET 703 may be switched to the non-conductive state. In such a case, two of the feedback capacitance 431, the feedback capacitance 432, and the feedback capacitance 433 operate as one feedback capacitance, and can output voltage pulses corresponding to the electric charges output from the X-ray detection element 31, without being saturated.

With this structure, the photon-counting CT detection circuitry 41 can output accurate count values for the respective energy bins, based on the voltage pulses output from at least one of the feedback capacitance 431, the feedback capacitance 432, and the feedback capacitance 433.

Otherwise, each of the n-type MOSFET 701, the n-type MOSFET 702, and the n-type MOSFET 703 is switched between the conductive state and the non-conductive state, in accordance with the magnitude of the tube voltage or the tube current supplied to the X-ray tube 221. The magnitude of the tube voltage or the tube current supplied to the X-ray tube 221 correlates with the magnitude of the electric charges output from the X-ray detection element 31 and the magnitude of the voltage amplified by the first amplifier 41a.

For example, when large tube voltage is supplied to the X-ray tube 221, the n-type MOSFET 701, the n-type MOSFET 702, and the n-type MOSFET 703 are switched to the conductive state. In this manner, the feedback capacitance 431, the feedback capacitance 432, and the feedback capacitance 433 operate as one feedback capacitance, and can output voltage pulses corresponding to the electric charges output from the X-ray detection element 31, without being saturated. With this structure, the photon-counting CT detection circuitry 41 can output accurate count values for the respective energy bins, based on the voltage pulses output from the feedback capacitance 431, the feedback capacitance 432, and the feedback capacitance 433 that operate as one feedback capacitance.

By contrast, when small tube voltage is supplied to the X-ray tube 221, the n-type MOSFET 701, the n-type MOSFET 702, or the n-type MOSFET 703 is switched to the conductive state. In this manner, the feedback capacitance 431, the feedback capacitance 432, or the feedback capacitance 433 can output voltage pulses corresponding to the electric charges output from the X-ray detection element 31, without being saturated. Otherwise, the n-type MOSFET 701, the n-type MOSFET 702, or the n-type MOSFET 703 may be switched to the non-conductive state. In such a case, two of the feedback capacitance 431, the feedback capacitance 432, and the feedback capacitance 433 operate as one feedback capacitance, and can output voltage pulses corresponding to the electric charges output from the X-ray detection element 31, without being saturated.

With this structure, the photon-counting CT detection circuitry 41 can output accurate count values for the respective energy bins, based on the voltage pulses output from at least one of the feedback capacitance 431, the feedback capacitance 432, and the feedback capacitance 433.

Each of the feedback capacitance 431, the feedback capacitance 432, and the feedback capacitance 433 has a desired capacitance. In addition, the number of feedback capacitances included in the detection circuitry 4z is not specifically limited.

Figure 16:
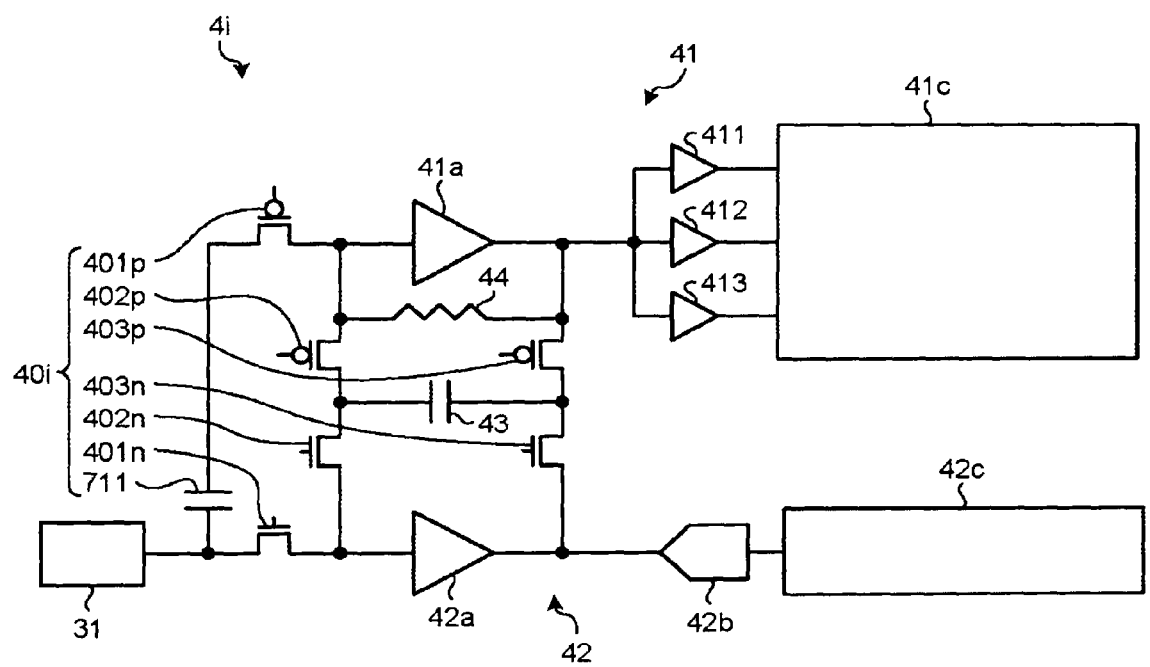
FIG. 16 is a diagram illustrating another example of the detection circuitry according to the first embodiment.

Otherwise, the photon-counting X-ray CT apparatus 1 may include detection circuitry 4i illustrated in FIG. 16, instead of the detection circuitry 4 illustrated in FIG. 3. The detection circuitry 4i includes switching circuitry 40i illustrated in FIG. 16, instead of the detection circuitry 4 illustrated in FIG. 3. As illustrated in FIG. 16, the switching circuitry 40i is obtained by adding a capacitor 711 to the switching circuitry 40 illustrated in FIG. 3. Specifically, the switching circuitry 40i includes a capacitor 711 that is installed between the X-ray detection element 31 and the first amplifier 41a that amplifies the voltage generated by the electric charges output from the X-ray detection element 31.

As illustrated in FIG. 16, the capacitor 711 is installed between the X-ray detection element 31 and the p-type MOSFET 401p. The capacitor 711 prevents a direct-current component that is output from the X-ray detection element 31 from flowing into the first amplifier 41a. With this structure, the voltage pulse that is output from the feedback capacitance 43 is not influenced by the direct-current component output from the X-ray detection element 31. With this structure, the detection circuitry 4i can detect accurate count values for the respective energy bins. The direct-current component that is output from the X-ray detection element 31 is a dark current, for example.

Figure 17:
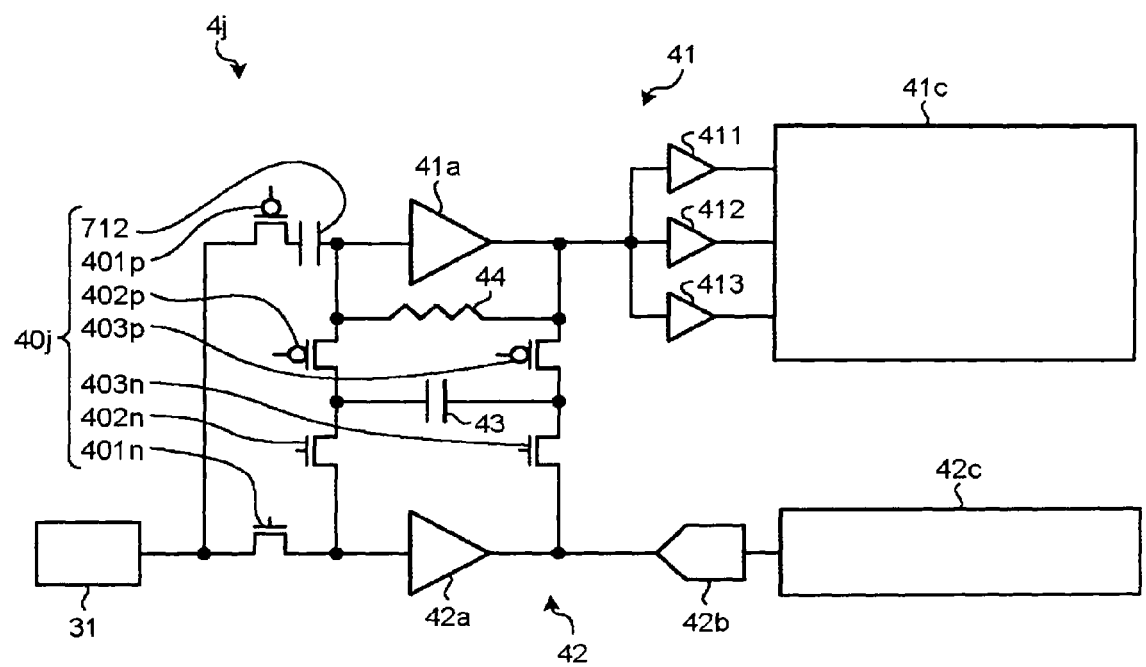
FIG. 17 is a diagram illustrating another example of the detection circuitry according to the first embodiment.

Otherwise, the photon-counting X-ray CT apparatus 1 may include detection circuitry 4j illustrated in FIG. 17, instead of the detection circuitry 4 illustrated in FIG. 3. The detection circuitry 4j includes switching circuitry 40j illustrated in FIG. 17, instead of the detection circuitry 4 illustrated in FIG. 3. As illustrated in FIG. 17, the switching circuitry 40j is obtained by adding a capacitor 712 to the switching circuitry 40 illustrated in FIG. 3. Specifically, the switching circuitry 40j includes a capacitor 712 that is installed between the X-ray detection element 31 and the first amplifier 41a that amplifies the voltage generated by the electric charges output from the X-ray detection element 31.

As illustrated in FIG. 17, the capacitor 712 is installed between the p-type MOSFET 401p and the first amplifier 41a, the feedback capacitance 43, and the resistor 44. The capacitor 712 has the same function as that of the capacitor 711 described above. With the capacitor 712, the detection circuitry 4j produces the same effect as that of the detection circuitry 4i.

An example of the processing performed by the photon-counting X-ray CT apparatus 1 according to the first embodiment has been explained above. As described above, the photon-counting X-ray CT apparatus 1 performs peak shift correction to correct the count values of the first counter 41c for each of the detection circuitry 4, and count value correction to correct the count values of the second counter 42c using the count values of the first counter 41c for each of the detection circuitry 4. With this structure, the photon-counting X-ray CT apparatus 1 prevents fluctuations in the energies of the photons detected by the respective detection circuitry 4, due to variations of the feedback capacitances 43 included in the respective detection circuitry 4. With this structure, the photon-counting X-ray CT apparatus 1 can acquire images with high contrast resolution.

In addition, because the photon-counting X-ray CT apparatus 1 includes the switching circuitry 40, the photon-counting CT detection circuitry 41, and the integral X-ray CT circuitry 42, the photon-counting X-ray CT apparatus 1 can perform photon-counting CT imaging or integral CT imaging alone. Besides, because the photon-counting X-ray CT apparatus 1 has the structure in which the feedback capacitance 43 is shared between the first amplifier 41a and the second amplifier 42a, the circuitry structure of the detection circuitry 4 can be made compact.

The detection circuitry included in the photon-counting X-ray CT apparatus 1 may include no feedback capacitance 43 shared between the first amplifier 41a and the second amplifier 42a. In such a case, the photon-counting CT detection circuitry and the integral CT detection circuitry include respective dedicated feedback capacitances, and have the following specific structures.

The photon-counting CT detection circuitry includes the first counter and the first amplifier. The first counter counts voltage pulses that are output from the feedback capacitance based on the electric charges output from the X-ray detection element that converts the incident X-rays into electric charges, for each of a plurality of energy bins that are set on the energy spectrum of the X-rays. The input terminal of the first amplifier is connected to the X-ray detection element, and the output terminal thereof is connected to the first counter. The integral CT detection circuitry includes the second counter and the second amplifier. The second counter counts voltage pulses that are output from the feedback capacitance based on the electric charges output from the X-ray detection element. The input terminal of the second amplifier is connected to the X-ray detection element, and the output terminal thereof is connected to the second counter. The switching circuitry switches between the case of transmitting the electric charges output from the X-ray detection element to the photon-counting CT detection circuitry and the case of transmitting the electric charges output from the X-ray detection element to the integral CT detection circuitry.

In addition, in such a case, the count value correction circuitry calculates the count values for the respective energy bins in the case where the integral CT detection circuitry operates, from the count value of the second counter and the count values for the respective energy bins obtained by the first counter, and corrects the count value of the second counter based on the count values.

The detection circuitry also can perform peak shift correction and count value correction, in the photon-counting X-ray CT apparatus 1 with the structure in which the photon-counting CT detection circuitry and the integral CT detection circuitry include respective dedicated feedback capacitances. Also in such a case with the structure, the photon-counting X-ray CT apparatus 1 can acquire images with high contrast resolution. The photon-counting X-ray CT apparatus 1 can also perform photon-counting CT imaging or integral CT imaging alone.

Second Embodiment

Figure 18:
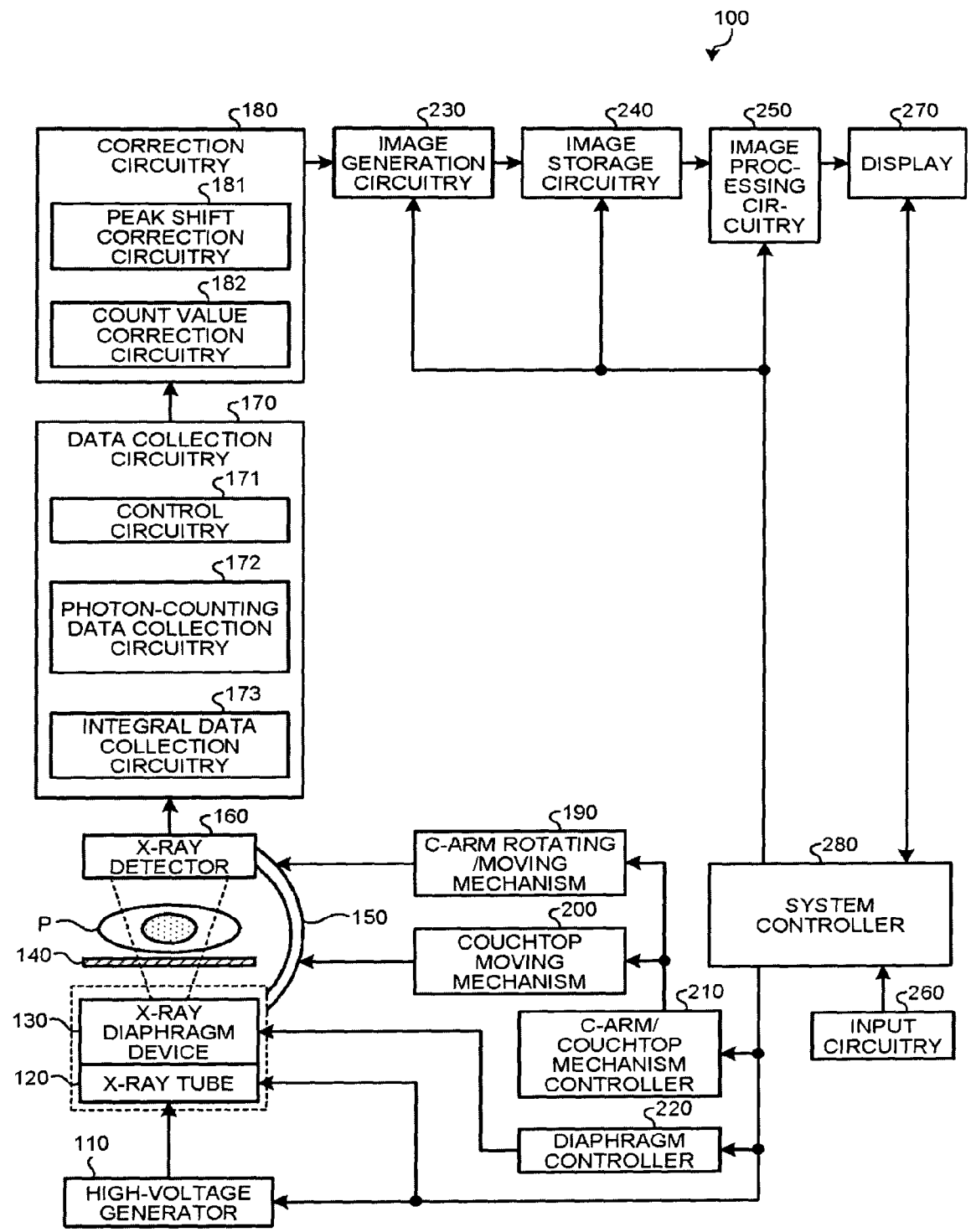
FIG. 18 is a diagram illustrating a configuration of a photon-counting X-ray diagnostic apparatus according to a second embodiment.

A configuration of a photon-counting X-ray diagnostic apparatus according to the second embodiment will be explained hereinafter, with reference to FIG. 18. FIG. 18 is a diagram illustrating the configuration of a photon-counting X-ray diagnostic apparatus 100 according to the second embodiment. As illustrated in FIG. 18, the photon-counting X-ray diagnostic apparatus 100 includes a high-voltage generator 110, an X-ray tube 120, an X-ray diaphragm device 130, a couchtop 140, a C-arm 150, an X-ray detector 160, a data collection circuitry 170, a correction circuitry 180, a C-arm rotating/moving mechanism 190, a couchtop moving mechanism 200, a C-arm/couchtop mechanism controller 210, a diaphragm controller 220, an image generation circuitry 230, an image storage circuitry 240, an image processing circuitry 250, an input circuitry 260, a display 270, and a system controller 280.

The high-voltage generator 110 supplies a tube voltage to the X-ray tube 120. The X-ray tube 120 generates X-rays to be applied to the subject P, with the tube voltage supplied from the high-voltage generator 110. The high-voltage generator 110 regulates the voltage supplied to the X-ray tube 120, to regulate the X-ray dose applied to the subject P, and control turning on/off of X-ray application to the subject P. The X-ray diaphragm device 130 is a device to narrow down the X-rays generated by the X-ray tube 120 to be selectively applied to the region of interest of the subject P. For example, the X-ray diaphragm device 130 includes four slidable diaphragm blades, to narrow down the X-rays generated by the X-ray tube 120 by sliding the diaphragm blades. The couchtop 140 is a bed on which the subject P is placed.

The C-arm 150 is a curved member to hold the X-ray tube 120, the X-ray diaphragm device 130, and the X-ray detector 160. The X-ray tube 120 and the X-ray diaphragm device 130 are arranged so as to oppose the X-ray detector 160 with the subject P interposed therebetween, using the C-arm 150.

The X-ray detector 160 is a multi-row detector including a plurality of X-ray detection elements arranged in a matrix. Each of the X-ray detection elements is installed with detection circuitry to detect energy of photons of the X-rays made incident on the X-ray detection element. The structure and operation of each of the X-ray detection elements are the same as those of each of the X-ray detection elements according to the first embodiment. Each of the detection circuitry includes switching circuitry, photon-counting imaging detection circuitry, and integral imaging detection circuitry. The structure and operation of the switching circuitry are the same as those of the switching circuitry according to the first embodiment. The structure and operation of the photon-counting imaging detection circuitry are the same as those of the photon-counting CT detection circuitry according to the first embodiment. The structure and operation of the integral imaging detection circuitry are the same as those of the integral CT detection circuitry according to the first embodiment. Specifically, a feedback capacitance is connected with the photon-counting imaging detection circuitry and the integral imaging detection circuitry in parallel.

The data collection circuitry 170 includes control circuitry 171, a photon-counting data collection circuitry 172, and an integral data collection circuitry 173.

The control circuitry 171 transmits switching signals to the switching circuitry. Specifically, the control circuitry 171 transmits switching signals to gate terminals of six MOSFETs included in the switching circuitry. The switching signals include a photon-counting imaging ON signal to control the switching circuitry to transmit the electric charges output from the X-ray detection element to the photon-counting imaging detection circuitry, and an integral imaging ON signal to control the switching circuitry to transmit the electric charges output from the X-ray detection element to the integral imaging detection circuitry, in each X-ray application. The operations of the six MOSFETs that have received switching signals are the same as those of the six MOSFETs according to the first embodiment.

The photon-counting data collection circuitry 172 collects the count values of the first counter, when the electric charges output from the X-ray detection element are transmitted to the photon-counting imaging detection circuitry by the switching circuitry. The count values collected by the photon-counting data collection circuitry 172 are transmitted to the correction circuitry 180 described later. As described above, the count values of the first counter are results of counting the voltage pulses that are output from the feedback capacitance for the respective energy bins that are set on the energy spectrum of the X-rays.

The integral data collection circuitry 173 collects the count value of the second counter, when the electric charges output from the X-ray detection element are transmitted to the integral imaging detection circuitry by the switching circuitry. The count value collected by the integral data collection circuitry 173 is transmitted to the correction circuitry 180 described later. As described above, the count value of the second counter is a result of counting the voltage pulses that are output from the feedback capacitance regardless of the energy bins that are set on the energy spectrum of the X-rays.

The correction circuitry 180 includes a peak shift correction circuitry 181 and a count value correction circuitry 182.

The peak shift correction circuitry 181 adds a certain energy value to the energy of the photons detected by the photon-counting imaging detection circuitry such that a count value of the first counter in the energy bin of the energy spectrum of the X-rays made incident on the X-ray detection element falls within a predetermined range including the count value of the first counter in an energy bin including the peak generated by the characteristic X-rays of a reference X-ray energy spectrum. The count value correction circuitry 182 performs correction after the correction performed by the peak shift correction circuitry 181.

Otherwise, the peak shift correction circuitry 181 adds a certain energy value to the energy of the photons detected by the photon-counting imaging detection circuitry such that the sum of squares, over the energy bins, of a difference in a count value of the first counter between an energy bin of an reference X-ray energy spectrum and an energy bin of the energy spectrum of the X-rays made incident on the X-ray detection element has a minimum value. The count value correction circuitry 182 performs correction after the correction performed by the peak shift correction circuitry 181. The details of the corrections performed by the peak shift correction circuitry 181 will be described later.

The count value correction circuitry 182 calculates count values for the respective energy bins in the case where the integral imaging detection circuitry operates, from the count values of the second counter and the count values for the respective energy bins obtained by the first counter, and corrects the count values of the second counter based on the calculated count values. The details of the correction performed by the count value correction circuitry 182 will be described later.

The C-arm rotating/moving mechanism 190 is a mechanism to rotate and move the C-arm 150. The C-arm rotating/moving mechanism 190 is also capable of changing a source image receptor distance (SID) serving as the distance between the X-ray tube 120 and the X-ray detector 160. The C-arm rotating/moving mechanism 190 is also capable of rotating the X-ray detector 160 that is held by the C-arm 150.

The couchtop moving mechanism 200 is a mechanism to move the couchtop 140. The C-arm/couchtop mechanism controller 210 regulates rotation and movement of the C-arm 150 and movement of the couchtop 140, by controlling the C-arm rotating/moving mechanism 190 and the couchtop moving mechanism 200, under the control of the system controller 280 described later. The diaphragm controller 220 controls the irradiation range of the X-rays applied to the subject P, by regulating the aperture of the diaphragm blades included in the X-ray diaphragm device 130, under the control of the system controller 280 described later.

The image generation circuitry 230 generates an X-ray image based on the count value of the second counter corrected by the count value correction circuitry 182. The image storage circuitry 240 stores the X-ray image generated by the image generation circuitry 230. The image processing circuitry 250 performs various image processing on the X-ray image generated by the image generation circuitry 230. For example, the image processing circuitry 250 directly acquires the X-ray image from the image generation circuitry 230, to perform various image processing. Otherwise, for example, the image processing circuitry 250 acquires the X-ray image generated by the image generation circuitry 230 from the image storage circuitry 240, to perform various image processing. The image processing circuitry 250 can store the image data having been subjected to image processing in the image storage circuitry 240.

The input circuitry 260 is a mouse, a keyboard, a button, a trackball, a joystick, a foot switch, and others used by the user of the photon-counting X-ray diagnostic apparatus 100 to input various instructions and various settings. The input circuitry 260 transfers the instructions received from the user to the system controller 280 described later. The display 270 is a monitor that is referred to by the user. The display 270 displays the results of a variety of image processing, and graphical user interfaces (GUIs) to receive various settings from the user via the input circuitry 260, for example.

The system controller 280 controls operations of the whole photon-counting X-ray diagnostic apparatus 100. For example, the system controller 280 controls the high-voltage generator 110 in accordance with user's instructions transferred from the input circuitry 260, to regulate the voltage supplied to the X-ray tube 120 and thereby control the X-ray dose applied to the subject P and turning on/off of X-ray application to the subject P. For example, the system controller 280 also controls the C-arm/couchtop mechanism controller 210 in accordance with user's instructions, to regulate rotation and movement of the C-arm 150 and movement of the couchtop 140. For example, the system controller 280 also controls the diaphragm controller 220 in accordance with user's instructions, to regulate the aperture of the diaphragm blades included in the X-ray diaphragm device 130 and thereby control the irradiation range of the X-rays applied to the subject P.

For example, the system controller 280 also controls X-ray image generation processing performed by the image generation circuitry 230, and image processing performed by the image processing circuitry 250, in accordance with user's instructions. For example, the system controller 280 also performs control to cause the display 270 to display GUI for receiving user's instructions and image data stored in the image storage circuitry 240.

The photon-counting X-ray diagnostic apparatus 100 according to the second embodiment performs processing performed by the photon-counting X-ray CT apparatus 1 according to the first embodiment. The photon-counting X-ray diagnostic apparatus 100 may perform processing performed by the photon-counting X-ray CT apparatus 1 according to the first embodiment in each view, in each frame during X-ray application.

The photon-counting X-ray diagnostic apparatus 100 according to the second embodiment has been explained above. As described above, the photon-counting X-ray diagnostic apparatus 100 performs peak shift correction to correct the count values of the first counter for each of the detection circuitry, and count value correction to correct the count value of the second counter for each of the detection circuitry using the count values of the first counter. With this structure, the photon-counting X-ray diagnostic apparatus 100 prevents fluctuations in the energies of the photons detected by the respective detection circuitry, due to variations of the feedback capacitances included in the respective detection circuitry. With this structure, the photon-counting X-ray diagnostic apparatus 100 can acquire images with high contrast resolution.

In addition, because the photon-counting X-ray diagnostic apparatus 100 includes the switching circuitry, the photon-counting imaging detection circuitry, and the integral X-ray imaging circuitry, the photon-counting X-ray diagnostic apparatus 100 can perform photon-counting imaging or integral imaging alone. Besides, because the photon-counting X-ray diagnostic apparatus 100 has the structure in which the feedback capacitance is shared between the first amplifier and the second amplifier, the circuitry structure of the detection circuitry can be made compact.

Image Processing System

The embodiments described above illustrate the case where the data collection circuitry, the peak shift correction circuitry, and the count value correction circuitry perform various processing, but the embodiments are not limited thereto. For example, the processing described above may be performed by an image processing system including the data collection circuitry, the peak shift correction circuitry, and the count value correction circuitry. Examples of the image processing system are a workstation, an image storage device (image server) of a picture archiving and communication system (PACS), a viewer, and various devices of an electronic medical chart system. In such a case, for example, the image processing system collects projection data, photon-counting data, and integral data, and the like. The image processing system also acquires projection data generated by the projection data generator, photon-counting data collected by the photon-counting data collection circuitry, and integral data collected by the integral data collection circuitry, by receiving the data via a network from the photon-counting X-ray CT apparatus or the photon-counting X-ray diagnostic apparatus or receiving the data input by the user via a storage medium, and stores the data in the memory or the like. The image processing system may also perform various processing on the projection data, the photon-counting data, and the integral data stored in the memory or the like.

The respective constituent elements described above are of functionally conceptual, and are not necessarily needed to be configured physically as illustrated in the drawings. That is, the specific embodiments of distribution or integration of the constituent elements are not limited to those illustrated in the drawings, and the whole or a part thereof can be configured by being functionally or physically distributed or integrated in any unit according to various types of loads and usage. Furthermore, the whole or a part of the various processing functions performed in the respective constituent elements is implemented by a CPU and a program executed by the CPU. Alternatively, the whole or a part of the various processing functions performed in the respective constituent elements is implemented as hardware by wired logic.

At least one of the embodiments described above enables acquisition of images with high contrast resolution.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A photon-counting X-ray computed tomography (CT) apparatus, comprising:
   photon-counting CT detection circuitry configured to output count values for respective energy bins, based on voltage pulses output from a feedback capacitor, the voltage pulses being based on electric charges output from an X-ray detection element configured to detect incident X-rays;
   integral CT detection circuitry configured to output an integral value, based on the voltage pulses output from the feedback capacitor, the voltage pulses being based on the electric charges output from the X-ray detection element; and
   switching circuitry configured to switch between a case of transmitting the electric charges output from the X-ray detection element to the photon-counting CT detection circuitry and a case of transmitting the electric charges output from the X-ray detection element to the integral CT detection circuitry, wherein
   the feedback capacitor is connected with the photon-counting CT detection circuitry and the integral CT detection circuitry in parallel.

2. The photon-counting X-ray CT apparatus according to claim 1, further comprising first correction circuitry configured to calculate count values for the respective energy bins in a case where the integral CT detection circuitry operates, from the integral value and the output count values for the respective energy bins, and correct the integral value based on the calculated count values.

3. The photon-counting X-ray CT apparatus according to claim 2, further comprising second correction circuitry configured to add a certain energy value to an energy of photons detected by the photon-counting CT detection circuitry such that a count value that is output from the photon-counting CT detection circuitry in an energy bin of an energy spectrum of the X-rays incident on the X-ray detection element falls within a predetermined range including the count value output from the photon-counting CT detection circuitry in an energy bin including a peak generated by characteristic X-rays of a reference X-ray energy spectrum, wherein
   the first correction circuitry performs correction after correction performed by the second correction circuitry.

4. The photon-counting X-ray CT apparatus according to claim 2, further comprising second correction circuitry configured to add a certain energy value to an energy of photons detected by the photon-counting CT detection circuitry such that a sum of squares, over the energy bins, of a difference in a count value output from the photon-counting CT detection circuitry between an energy bin of a reference X-ray energy spectrum and an energy bin of an energy spectrum of the X-rays incident on the X-ray detection element has a minimum value, wherein
   the first correction circuitry performs correction after correction performed by the second correction circuitry.

5. The photon-counting X-ray CT apparatus according to claim 1, wherein the switching circuitry is configured to switch between the case of transmitting the electric charges output from the X-ray detection element to the photon-counting CT detection circuitry and the case of transmitting the electric charges output from the X-ray detection element to the integral CT detection circuitry, in each of a plurality of views.

6. The photon-counting X-ray CT apparatus according to claim 5, further comprising control circuitry configured to transmit switching signals to the switching circuitry, wherein
   the switching signals include, in each of the plurality of views, a photon-counting CT ON signal to control the switching circuitry to transmit the electric charges output from the X-ray detection element to the photon-counting CT detection circuitry, and an integral CT ON signal to control the switching circuitry to transmit the electric charges output from the X-ray detection element to the integral CT detection circuitry.

7. The photon-counting X-ray CT apparatus according to claim 6, wherein a period for which the photon-counting CT ON signal is transmitted is shorter than a period for which the integral CT ON signal is transmitted, in each of the plurality of views.

8. The photon-counting X-ray CT apparatus according to claim 6, wherein, in each of the plurality of views, the control circuitry shortens the period for which the photon-counting CT ON signal is transmitted, when photons of the X-rays incident on the X-ray detection element increase in number.

9. The photon-counting X-ray CT apparatus according to claim 1, wherein a plurality of feedback capacitors are connected with the photon-counting CT detection circuitry and the integral CT detection circuitry in parallel, and a feedback capacitor of the plurality of feedback capacitors used to output the voltage pulses is switched in accordance with a magnitude of the electric charges output from the X-ray detection element.

10. The photon-counting X-ray CT apparatus according to claim 1, wherein the switching circuitry further includes a capacitor installed between the X-ray detection element and a first amplifier, the first amplifier being connected with the feedback capacitor in parallel and configured to amplify a voltage generated by the electric charges output from the X-ray detection element.

11. A photon-counting X-ray computed tomography (CT) apparatus, comprising:
    photon-counting CT detection circuitry configured to output count values for respective energy bins, based on voltage pulses output from a feedback capacitor, the voltage pulses being based on electric charges output from an X-ray detection element configured to detect incident X-rays;
    integral CT detection circuitry configured to output an integral value, based on the voltage pulses output from the feedback capacitor, the voltage pulses being based on the electric charges output from the X-ray detection element;
    switching circuitry configured to switch between a case of transmitting the electric charges output from the X-ray detection element to the photon-counting CT detection circuitry and a case of transmitting the electric charges output from the X-ray detection element to the integral CT detection circuitry; and
    first correction circuitry configured to calculate count values for the respective energy bins in a case where the integral CT detection circuitry operates, from the integral value and the output count values for the respective energy bins, and correct the integral value based on the calculated count values.

12. A photon-counting X-ray diagnostic apparatus, comprising:
    photon-counting imaging detection circuitry configured to output count values for respective energy bins, based on voltage pulses output from a feedback capacitor, the voltage pulses being based on electric charges output from an X-ray detection element configured to detect incident X-rays;
    integral imaging detection circuitry configured to output an integral value, based on the voltage pulses output from the feedback capacitor, the voltage pulses being based on the electric charges output from the X-ray detection element; and
    switching circuitry configured to switch between a case of transmitting the electric charges output from the X-ray detection element to the photon-counting imaging detection circuitry and a case of transmitting the electric charges output from the X-ray detection element to the integral imaging detection circuitry, wherein
    the feedback capacitor is connected with the photon-counting imaging detection circuitry and the integral imaging detection circuitry in parallel.

* * * * *